United States Patent [19]

Dickinson et al.

[11] Patent Number: 5,618,941
[45] Date of Patent: Apr. 8, 1997

[54] BENZENEALKANOIC ACIDS FOR CARDIOVASCULAR DISEASES

[75] Inventors: Roger P. Dickinson; Kevin N. Dack; John Steele, all of Sandwich, United Kingdom

[73] Assignee: Pfizer Inc., New York, N.Y.

[21] Appl. No.: 397,063

[22] PCT Filed: Sep. 14, 1993

[86] PCT No.: PCT/EP93/02488

§ 371 Date: Mar. 15, 1995

§ 102(e) Date: Mar. 15, 1995

[87] PCT Pub. No.: WO94/06761

PCT Pub. Date: Mar. 31, 1994

[30] Foreign Application Priority Data

Sep. 23, 1992 [GB] United Kingdom ............... 9220137

[51] Int. Cl.⁶ .................. C07C 311/19; C07C 233/51; A61K 31/19
[52] U.S. Cl. .................. 546/249; 549/6; 549/504; 549/491; 549/497; 560/147; 560/157
[58] Field of Search .................. 560/147, 157; 549/491, 497, 504, 6; 546/249; 514/345, 354, 357, 445, 446, 448, 471, 473, 562, 563, 568

[56] References Cited

U.S. PATENT DOCUMENTS 4,258,058  3/1981  Witte et al. .............. 424/309
4,443,477  4/1984  Witte et al. .............. 424/319

FOREIGN PATENT DOCUMENTS 9217451  10/1992  WIPO .
9313057  7/1993  WIPO .

*Primary Examiner*—Porfirio Nazario-Gonzalez
*Assistant Examiner*—Dwayne C. Jones
*Attorney, Agent, or Firm*—Peter C. Richardson; Gregg C. Benson; A. Dean Olson

[57] ABSTRACT

Compounds of formula (I) wherein $R^1$, $R^2$, $R^3$ and $R^4$ are each H or $C_1$–$C_4$ alkyl; $R^5$ is $(CH_2)_m NHSO_2 R^6$ or $(CH)_m$-$NHCOR^6$; $R^6$ is $C_1$–$C_6$ alkyl, $C_3$–$C_6$ cycloalkyl optionally substituted by aryl, aryl or heteroaryl; $R^7$ is H, $C_1$–$C_4$ alkyl, $C_1$–$C_4$ alkoxy, halo, $CF_3$, $OCF_3$, CN, $CONH_2$, or $S(O)_n(C_1$–$C_4$ alkyl); X is $CH_2$, $CHCH_3$, CH(OH), $C(OH)CH_3$, C=$CH_2$, CO or O; m is 0 or 1 and n is 0, 1 or 2, and their pharmaceutically acceptable salts and biolabile esters, are antagonists of thromboxane $A_2$ of utility, particularly in combination with a thromboxane synthetase inhibitor, in the treatment of atherosclerosis and unstable angina and for prevention of reocclusion after percutaneous transluminal angioplasty.

17 Claims, No Drawings

BENZENEALKANOIC ACIDS FOR CARDIOVASCULAR DISEASES

This application is filed under 35 U.S.C. §371 based on PCT/EP93/02488, which was filed on Sep. 14, 1993 which claims priority from Great Britain application 9220137.5 which was filed on Sep. 23, 1992.

This invention relates to certain di-substituted benzenealkanoic acids. Such compounds are able to selectively antagonise the effect of thromboxane $A_2$ ($TXA_2$), and its precursor prostaglandin $H_2$ ($PGH_2$) at the thromboxane receptor. The compounds are thus useful as therapeutic agents and they may be used either alone, or preferably in combination with a thromboxane synthetase inhibitor, for example in the treatment of atherosclerosis and unstable angina and for prevention of reocclusion, both acute and chronic, after percutaneous transluminal coronary and femoral angioplasty. The combination may also find clinical utility in a further variety of disease conditions in which thromboxane $A_2$ has been implicated such as in the treatment of myocardial infarction, stroke, cardiac arrhythmias, transient ischaemic attack, tumour metastasis, peripheral vascular disease, bronchial asthma, renal disease, cyclosporin-induced neprotoxicity, renal allograft rejection, vascular complications of diabetes and endotoxin shock, trauma, pre-eclampsia and in coronary artery bypass surgery and haemodialysis.

The compounds of the invention are of formula:

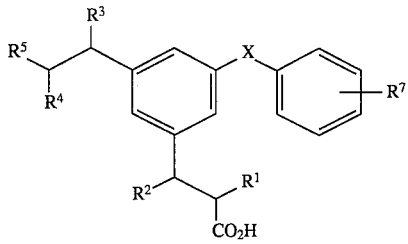

(I)

and pharmaceutically acceptable salts and biolabile esters thereof,
wherein $R^1$, $R^2$, $R^3$ and $R^4$ are each independently H or $C_1$–$C_4$ alkyl;

$R^5$ is $(CH_2)_m NHSO_2 R^6$ or $(CH_2)_m NHCOR^6$;

$R^6$ is $C_1$–$C_6$ alkyl, $C_3$–$C_6$ cycloalkyl optionally substituted by aryl, aryl or heteroaryl;

$R^7$ represents from one to three substituents each independently selected from H, $C_1$–$C_4$ alkyl, $C_1$–$C_4$ alkoxy, halo, $CF_3$, $OCF_3$, CN, $CONH_2$ and $S(O)_n(C_1$–$C_4$ alkyl);

X is $CH_2$, $CHCH_3$, CH(OH), C(OH)$CH_3$, C=$CH_2$, CO, or O;

m is 0 or 1;
and n is 0, 1 or 2.

In the above definition aryl means phenyl or naphthyl, and heteroaryl means furyl, thienyl or pyridyl, any of which ring systems may optionally be substituted with one to three substituents each independently chosen from $C_1$–$C_4$ alkyl, $C_1$–$C_4$ alkoxy, halo, $CF_3$, $OCF_3$ and CN. Unless otherwise indicated, alkyl and alkoxy groups having three or more carbon atoms may be straight-chain or branched-chain. Halo means fluoro, chloro, bromo or iodo.

Compounds containing asymmetric centres can exist as enantiomers and diastereisomers, and the invention includes the separated individual isomers as well as mixtures of isomers.

Also included in the invention are radiolabelled derivatives of compounds of formula (I) which are suitable for biological studies.

The term biolabile ester in the above definition means a pharmaceutically acceptable, biologically degradable ester derivative of a compound of formula (I), that is a prodrug which, upon administration to an animal or human being, is converted in the body to a compound of formula (I). In the case of the compounds of formula (I), such biolabile ester prodrugs are particularly advantageous in providing compounds of formula (I) suitable for oral administration. The suitability of any particular ester-forming group can be assessed by conventional in vivo animal or in vitro enzyme hydrolysis studies. Thus desirably, for optimum effect, the ester should only be hydrolysed after absorption is complete. Accordingly, the ester should be resistant to premature hydrolysis by digestive enzymes before absorption, but should be productively hydrolysed by, for example, gutwall, plasma or liver enzymes. In this way, the active acid is released into the bloodstream following oral absorption of the prodrug.

Suitable biolabile esters may include alkyl, alkanoyloxyalkyl, cycloalkanoyloxyalkyl, aroyloxyalkyl and alkoxycarbonyloxyalkyl esters, including cycloalkyl and aryl substituted derivatives thereof, aryl esters and cycloalkyl esters, wherein said alkyl, alkanoyl or alkoxy groups may contain from 1 to 8 carbon atoms and be branched-chain or straight-chain, said cycloalkyl groups may contain from 3–7 carbon atoms and said cycloalkanoyl groups from 4–8 carbon atoms wherein both are optionally benzo-fused, and said aryl and aroyl groups include substituted phenyl, naphthyl or indanyl ring systems. Preferably, the biolabile esters of the invention are $C_1$–$C_4$ alkyl esters. More preferably, they are methyl, ethyl and t-butyl esters.

The pharmaceutically acceptable salts of the compounds of formula (I) are those formed with bases which provide non-toxic salts. Examples include the alkali and alkaline earth metal salts such as the sodium, potassium or calcium salts, and salts with amines such as diethylamine.

A preferred group of compounds of formula (I) is that wherein $R^1$, $R^2$, $R^3$ and $R^4$ are each H, $R^5$ is $NHSO_2R^6$ and X is $CH_2$, $CH(CH_3)$, CO or O. $R^6$ is preferably phenyl substituted by halo or $CF_3$, most preferably 4-chlorophenyl. $R^7$ is preferably H, F, $OCH_3$; $SO_2CH_3$ or CN.

Particularly preferred compounds include-:

3-[(4-fluorophenyl)methyl]-5-[2-[(4-trifluoromethylphenyl)sulphonylamino]ethyl]benzenepropanoic acid;

3-[2-[(4-chlorophenyl)sulphonylamino]ethyl]-5-[1-(4-fluorophenyl)ethyl]benzenepropanoic acid;

3-[2-[(4-chlorophenyl)sulphonylamino]ethyl]-5-[(4-fluorophenyl)methyl]benzenepropanoic acid;

3-[2-[(4-chlorophenyl)sulphonylamino]ethyl]-5-(4-fluorophenoxy)benzenepropanoic acid;

3-[2-[(4-chlorophenyl)sulphonylamino]ethyl]-5-(4-methoxybenzoyl)benzenepropanoic acid; and 3-[2-[(4-chlorophenyl)sulphonylamino]ethyl]-5-(4-cyanobenzoyl)benzenepropanoic acid.

In another aspect the present invention provides processes for the preparation of compounds of formula (I), their biolabile esters and pharmaceutically accetable salts.

In one process, the compounds of formula (I) are obtained by hydrolysis of their lower alkyl ester precursors of formula (II):

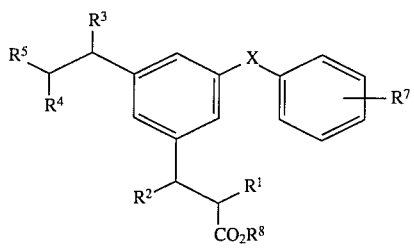

(II)

wherein $R^1$, $R^2$, $R^3$, $R^4$, $R^5$, $R^7$, and X are as previously defined for formula (I), and $R^8$ is $C_1$–$C_4$ alkyl, preferably methyl, ethyl or t-butyl.

The reaction can be conducted under basic or acidic conditions, e.g. with excess aqueous alkali, preferably sodium hydroxide solution, or excess hydrochloric acid respectively, optionally with a suitable co-solvent such as a $C_1$–$C_4$ alkanol, preferably methanol, at from about 20° C. to the reflux temperature of the reaction medium.

Certain compounds of the general formula (I) may also be converted to other compounds of formula (I) by standard functional group interconversions. For example, compounds of the formula (I) wherein $R^7$ is 2-F, 2-Cl, 4-F or 4-Cl and X is CO may be converted to the corresponding compounds where $R^7$ is 2-($C_1$–$C_4$)alkoxy or 4-($C_1$–$C_4$)alkoxy by treatment with an alkali metal alkoxide in a suitable solvent, such as N,N-dimethylformamide or an excess of the ($C_1$–$C_4$)alkanol, at temperatures up to the boiling point of the solvent. The same interconversion may also be carried out by heating the fluoro or chloro compound in an excess of the $C_1$–$C_4$ alkanol in the presence of a base such as sodium or potassium carbonate.

Compounds of the general formula (I) wherein X is CO and $R^7$ is 2- or 4-($C_1$–$C_4$)alkylthio may also be prepared from the corresponding compounds wherein $R^7$ is 2-F, 2-Cl, 4-F or 4-Cl by treatment with an alkali metal ($C_1$–$C_4$)alkylthiolate salt in a suitable solvent such as N,N-dimethylformamide or dimethylsulphoxide at a temperature of 50°–150° C. Similarly use of an alkali metal ($C_1$–$C_4$)alkylsulphimate in a solvent such as N,Ndimethylformamide or dimethylsulphoxide at a temperature of 50°–150° C. gives the corresponding compound of formula (I) wherein $R^7$ is ($C_1$–$C_4$)-alkylsulphonyl.

Compounds of the formula (I) wherein $R^7$ is $SO_2$($C_1$–$C_4$)alkyl may also be prepared by oxidation of the corresponding compound wherein $R^7$ is S($C_1$–$C_4$)alkyl using for example, hydrogen peroxide in a suitable solvent such as acetic acid. Controlled oxidation using, for example, a stoichiometric amount of hydrogen peroxide in acetic acid, or sodium metaperiodate in aqueous methanol affords the corresponding compounds of the formula (I) wherein $R^7$ is SO($C_1$–$C_4$)alkyl.

Compounds of the general formula (I) where $R^7$ is $CONH_2$ are preferably prepared from the corresponding compound where $R^7$ is CN by treatment with hydrogen peroxide and aqueous base (e.g. sodium hydroxide), typically at a temperature of about 50° C. Ethanol may be added as a co-solvent. The amide product may be converted to the corresponding compound where $R^7$ is $NH_2$ using the Hofmann reaction, i.e. by treatment with sodium hypochlorite under aqueous alkaline conditions. The amino compounds are useful intermediates for certain other compounds of the formula (I). For example, diazotisation followed by treatment with cuprous chloride or cuprous bromide gives the corresponding products where $R^7$ is Cl and Br, respectively. Alternatively, treatment of the diazonium compound with an iodide salt such as potassium iodide gives the corespending product of formula (I) where $R^7$ is I. This is a preferred approach to compounds of formula (I) where $R^7$ is Br or I since the latter substituents would react at several of the intermediate stages described later for the preparation of other compounds of the formula (I).

Compounds of the formula (I) wherein X is CO and $R^7$ is 2-CN or 4-CN may be obtained by treatment of the corresponding compound wherein $R^7$ is 2-F, 2-Cl, 4-F or 4-Cl with an alkali metal cyanide in a suitable solvent such as N,N-dimethylformamide or dimethylsulphoxide at temperatures of from 50°–150° C.

Compounds of the formula (I) wherein X is $CH_2$ and $R^1$, $R^2$, $R^3$, $R^4$ and $R^7$ are as previously defined may also be prepared by reduction of the corresponding compound wherein X is CO or CH(OH) using triethylsilane in trifluoroacetic acid. In addition, compounds of the formula (I) wherein X is CHOH and $R^1$, $R^2$, $R^3$, $R^4$ and $R^7$ are as previously defined may also be prepared by reduction of the corresponding compound wherein X is CO using sodium borohydride in a suitable solvent such as methanol or ethanol.

Compounds of the formula (I) wherein X is CO may also be obtained by oxidation of the corresponding compound wherein X is CHOH. The oxidation may be carried out using, for example, oxalyl chloride and dimethyl sulphoxide in dichloromethane (Swern oxidation).

Depending on the nature of $R^5$ and X, the compounds of formula (II) can be obtained in a variety of ways as described below-:

When $R^5$ is $(CH_2)_m NHSO_2 R^6$ or $(CH_2)_m NHCOR^6$, wherein $R^6$ and m are as previously defined for formula (I), such compounds of formula (II) may be obtained by sulphonylation or acylation respectively of an amine of formula (III):

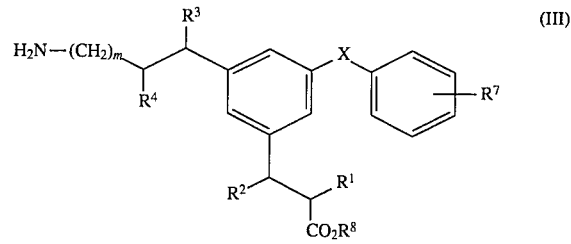

(III)

wherein m is 0 or 1, and $R^1$, $R^2$, $R^3$, $R^4$, $R^7$, $R^8$ and X are as previously defined for formula (II). The sulphonylation can be carried out by reacting an amine of formula (III) with a sulphonic anhydride of formula $(R^6SO_2)_2O$ or a sulphonyl halide (preferably chloride) of formula $R^6SO_2$halo, wherein halo and $R^6$ are as previously defined. For the acylation, either the appropriate acid anhydride of formula $(R^6CO)_2O$ or acyl halide (preferably chloride) of formula $R^6CO$halo, wherein halo and $R^6$ are as previously defined, is employed. These reactions are generally conducted in the presence of excess tertiary amine such as triethylamine, 4-dimethylaminopyridine (DMAP) or pyridine to act as acid scavenger, optionally in the presence of DMAP as catalyst when it is not used as acid scavenger, in a suitable solvent such as dichloromethane, at from about –75° to about 40° C. Alternatively, pyridine can be used to act as both acid scavenger and solvent.

Acylation may also be carried out using an acyl imidazolide in a solvent such as tetrahydrofuran or dioxan. Alternatively, standard peptide coupling methodology may be used and, in a typical procedure, a mixture of the amine of formula (III) and a carboxylic acid of formula $R^6CO_2H$ are treated with 1-(3-dimethylaminopropyl)-3-ethylcarbodiimide hydrochloride, 1-hydroxybenzotriazole and a base such as N,N-diethylisopropylamine in a suitable solvent such as dichloromethane.

Compounds of the general formula (II) wherein $R^1$, $R^2$, $R^3$, $R^4$, $R^5$, $R^7$ and X are as previously defined may also be obtained by esterification of a compound of the general formula (I) using an alcohol of the formula $R^8OH$ in the presence of an acidic catalyst such as hydrogen chloride or sulphuric acid.

Compounds of the general formula (II) may also be obtained using functional group interconversion reactions as described above for the preparation of compounds of the general formula (I). For example, compounds wherein X is CO may be reduced to give compounds wherein X is CHOH or $CH_2$, and compounds wherein X is CHOH may be oxidised to give compounds wherein X is CO. Also, in the case where X is CO, nucleophilic displacement of a 2-F, 2-Cl, 4-F or 4-Cl group may be carried to give, for example, the corresponding compound where $R^7$ is 2-CN or 4-CN as previously described.

Compounds of the formula (II) wherein X is $CHCH_3$ are obtainable by reduction of the corresponding compound of formula (II) wherein X is $C=CH_2$. This may be achieved by catalytic hydrogenation using a palladium on charcoal catalyst in a suitable solvent such as ethanol. Compounds of formula (II) wherein X is $C=CH_2$ may, in turn, be synthesised by dehydration of the corresponding compound of formula (II) wherein X is $C(OH)CH_3$, by treating this tertiary alcohol with an acid such as trifluoroacetic acid at about 50° C.

The above compounds of formulae (II) and (III) also form part of the invention. The former may be active in vivo by virtue of esterase-mediated hydrolysis to liberate the corresponding acid of formula (I), whilst the latter are key intermediates.

In an alternative process, compounds of formula (I) wherein $R^1$, $R^2$, $R^3$, $R^4$, $R^7$ and X are as previously defined, and m is 0 may be prepared from compounds of formula (IV) by a 'one pot' procedure in which the amide undergoes a Hofmann degradation in the presence of sodium hypochlorite and an aqueous base (for example sodium hydroxide) in a solvent such as dioxan or tetrahydrofuran. The resulting amine is then treated, without isolation, with a suitable sulphonylating or acylating agent as previously defined. The excess base serves as both an acid scavenger in the sulphonylation or acylation, and causes in situ hydrolysis of the ester to the corresponding acid of formula (I).

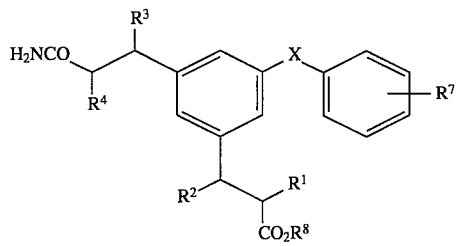

(IV)

Compounds of formula (III), wherein m is 0 and $R^1$, $R^2$, $R^3$, $R^4$, $R^7$, $R^8$ and X are as previously defined for formula (III), may be obtained from the corresponding carbamates of formula (V):

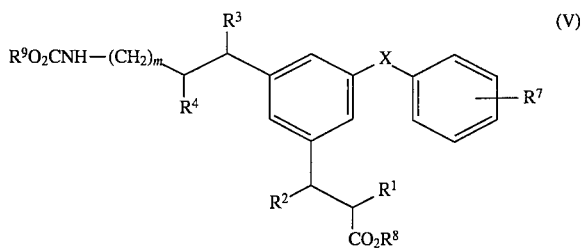

(V)

wherein $R^9$ is a group which can be selectively removed in the presence of $R^s$, e.g. benzyl or t-butyl, m is 0, and $R^1$, $R^2$, $R^3$, $R^4$, $R^7$, $R^8$ and X are as previously defined for formula (III). When $R^9$ is benzyl, amine deprotection is preferably effected by catalytic transfer hydrogenation of the substrate using ammonium formate and palladium on charcoal catalyst in a suitable solvent, e.g. a methanol-tetrahydrofuran mixture, at the reflux temperature of the reaction medium. Alternatively, when $R^9$ is t-butyl, either hydrogen chloride or trifluoroacetic acid in a suitable solvent, e.g. dichloromethane, at from about 0° to about 20° C., can be used to achieve the required deprotection.

Compounds of formula (V), wherein m is and $R^1$, $R^2$, $R^3$, $R^4$, $R^7$, $R^8$, $R^9$ and X are as previously defined for formula (V), can be synthesised directly, in a one-pot process, from the carboxylic acids of formula (VIa):

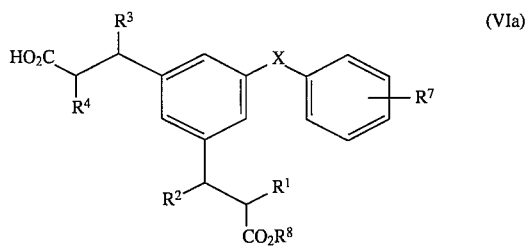

(VIa)

wherein $R^1$, $R^2$, $R^3$, $R^4$, $R^7$, $R^8$ and X are as previously defined for formula (V). The reaction is carried out by heating, under reflux, a solution of a compound of formula (VIa), an "azide-transfer reagent" such as diphenylphosphoryl azide, a tertiary amine such as triethylamine and excess of the required alcohol of formula $R^9OH$, e.g. benzyl alcohol or t-butanol, in an inert solvent such as 1,4-dioxane; alternatively, the excess alcohol may itself suffice as a suitable solvent. In the first phase of the reaction the acyl azide derivative of (VIa) is produced which, under the reaction conditions, undergoes a Curtius rearrangement to generate the intermediate isocyanate. The latter is then trapped in situ by the attendant benzyl alcohol or t-butanol to afford either the benzyl or t-butyl carbamate respectively of formula (V).

Compounds of formula (IV) wherein $R^1$, $R^2$, $R^3$, $R^4$, $R^7$ and $R^8$ are as previously defined for formula (II), can by synthesised from the carboxylic acids of the formula (VIa) by conversion to an activated form, e.g. the acid chloride, by treatment with, for example, oxalyl chloride, thionyl chloride or phosphorous pentachloride, followed by reaction with ammonia in a suitable solvent such as diethyl ether or acetone.

Alternatively, compounds of formula (IV) can be synthesised by hydrogenation of a compound of the formula (VII).

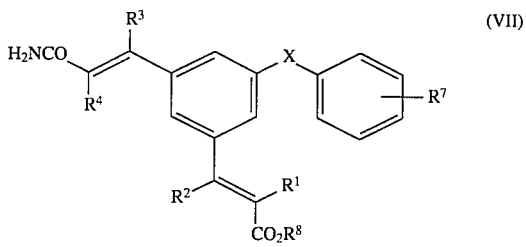

The hydrogenation is carried out in the presence of a catalyst such as palladium on carbon in a suitable solvent such as ethanol, ethyl acetate or acetic acid at pressures of from 1 to 10 atmospheres and a temperature of from 20°–100° C. Alternatively, catalytic transfer hydrogenation may be used, employing the conditions described for the conversion of (V) to (III). In a variant of the above process, hydrogenation of the amide of formula (VII) wherein $R^1$, $R^2$, $R^3$, $R^4$, $R^7$ and $R^8$ are as previously defined, and X is $CH(OCOR^{10})$ where $R^{10}$ is $C_1$–$C_4$ alkyl or phenyl, results in simultaneous reduction of the double bonds and hydrogenolysis of the acyloxy substituent to give the corresponding compound of formula (IV) where X is $CH_2$. Similarly, hydrogenation of the amide of formula (VII) wherein X is $C=CH_2$, results in simultaneous reduction of all double bonds to give the product of formula (IV) where X is $CH(CH_3)$. In cases where, for example, $R^8$ is methyl or ethyl, the monoacid intermediates of formula (VIa) are obtainable from diesters of formula (VIIIa):

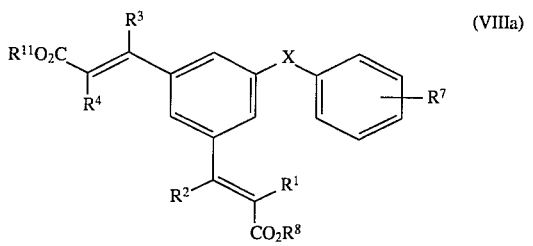

wherein $R^{11}$ is a group, for example t-butyl, which can be selectively removed in the presence of $R^8$, $R^8$ is methyl or ethyl, and $R^1$, $R^2$, $R^3$, $R^4$, $R^7$, and X are as previously defined for formula (VIa).

Prior to this selective ester deprotection, the two alkenyl groups are concurrently reduced, preferably by catalytic transfer hy. drogenation, which may be effected using the conditions described above for the conversion of (V) to (III) when $R^9$ is benzyl, but preferably at a temperature of about 60° C. Alternatively, conventional hydrogenation in a suitable solvent e.g. ethanol, ethyl acetate or acetic acid, in the presence of a catalyst such as palladium on carbon may be used. This step is followed by removal of the t-butyl group ($R^{11}$) using, for example, hydrogen chloride or trifluoroacetic acid at from about 0° to about 20° C. in a solvent such as dichloromethane. Clearly, in cases where $R^{11}$ is benzyl, reduction of the two alkenyl groups and removal of $R^{11}$ is achievable in one step under, for example catalytic transfer hydrogenation conditions.

In cases where, for example, $R^8$ is t-butyl, (VIa) can be obtained from (VIIIa) by again ensuring that $R^{11}$ can be selectively removed in the presence of $R^8$, e.g. where $R^{11}$ is methyl or ethyl. Thus, after reduction of the two alkenyl groups, base hydrolysis under mild conditions is effected using, for example, about one equivalent of an inorganic base such as sodium hydroxide or potassium hydroxide in aqueous 1,4-dioxane as solvent at from about 20° to about 100° C.

In an alternative approach, compounds of the formula (IV) wherein $R^1=R^4$ and $R^2=R^3$, and $R^7$, $R^8$, and X and m are as previously defined and may also be synthesised from monoacids of the formula (VIb):

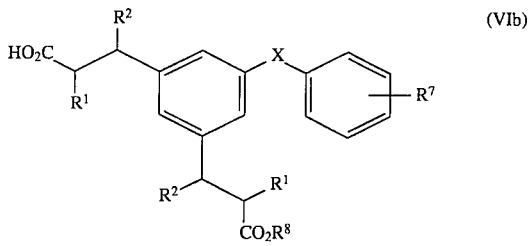

wherein $R^1$, $R^2$, $R^7$, $R^8$ and X are as previously defined, by processes analogous to those described above for the conversion of (VIa) to (IV).

Also, compounds of the formula (V) wherein $R^1=R^4$ and $R^2=R^3$ and $R^8$, $R^9$, X and m are as previously defined for formula (V), may be synthesised from monoacids of formula (VIb). The monoacids of formula (VIb) are also obtained in a two-step procedure from the symmetrical unsaturated diesters of formula (VIIIb):

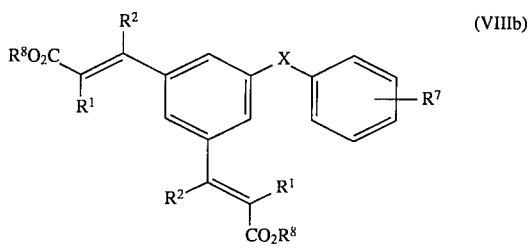

wherein $R^1$, $R^2$, $R^7$, $R^8$ and X are as previously defined for formula (VIb), by catalytic transfer hydrogenation, or conventional hydrogenation as described previously to give the corresponding diester (IX);

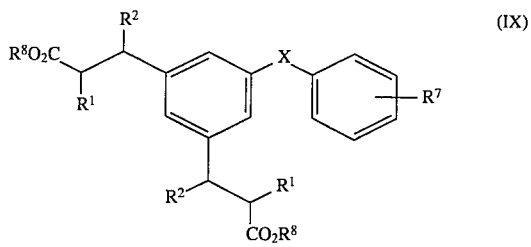

followed by selective ester deprotection, preferably via base hydrolysis using, for example, about one equivalent of inorganic base such as sodium hydroxide or potassium hydroxide in aqueous solution together with an appropriate co-solvent, at from about 20° C. to the reflux temperature of the reaction medium.

Clearly, this alternative approach is also applicable in cases where $R^1=R^2=R^3=R^4$.

In a variant of the above, hydrogenation of the diester of formula VIIIb wherein $R^1$, $R^2$, $R^7$ and $R^8$ are as previously defined, and X is $CH(OCOR^{10})$ where $R^{10}$ is $C_1$–$C_4$ alkyl or phenyl, results in simultaneous reduction of the double bonds and hydrogenolysis of the acyloxy substituent.

Compounds of formula (III), wherein m is 1 and $R^1$, $R^2$, $R^3$, $R^4$, $R^7$, $R^8$ and X are as previously defined for formula (III), may be obtained by direct reduction of compounds of formula (VIIIc):

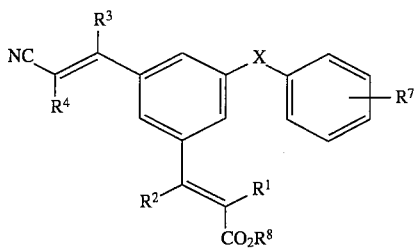

wherein $R^1$, $R^2$, $R^3$, $R^4$, $R^7$, $R^8$ and X are as previously defined for formula (III). The one-step reduction of the nitrile group and both alkenyl groups of (VIIIc) may be achieved by a cobalt(II)-mediated process, in which a mixture of cobalt(II) chloride, sodium borohydride and the substrate of formula (VIIIc), in a suitable solvent, e.g. ethanol, is allowed to react at about 0° C.

Compounds of formula (VIIIa) may be obtained by a variety of synthetic procedures, depending on the nature of X. For example, when X is $CH_2$, CH(OH), C(OH)$CH_3$, CO or O, and $R^1$, $R^2$, $R^3$, $R^4$, $R^8$ and $R^{11}$ are as previously defined for formula (VIIIa), they may be obtained from alkenoic esters of formula (X):

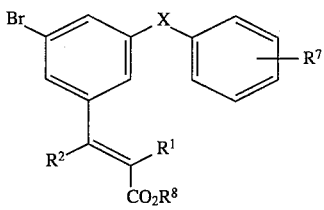

wherein X is $CH_2$, CH(OH), C(OH)$CH_3$, CO or O, and $R^1$, $R^2$, $R^7$ and $R^8$ are as previously defined for formula (VIIIa), using standard Heck reaction methodology. This involves treatment of (X) with excess alkenoic ester of formula (XI).

wherein $R^3$, $R^4$ and $R^{11}$ are as previously defined for formula (VIIIa), in the presence of palladium(II) acetate, tri-o-tolylphosphine and triethylamine, in a suitable solvent such as acetonitrile or dimethylformamide, at from about 80° to about 160° C.

Compounds of formula (VII) may be obtained from a compound of formula (X) wherein X is $CH_2$, CH(OH), C(OH)$CH_3$, CO or O and $R^1$, $R^2$, $R^7$ and $R^8$ are as previously defined for formula (VII) by treatment with an unsaturated amide of formula (XII):

wherein $R^3$ and $R^4$ are as previously defined, in the presence of palladium(II) acetate, tri-o-tolylphosphine and triethylamine, in a suitable solvent such as acetonitrile or dimethylformamide, at from about 80° to about 160° C. Under conditions of prolonged heating (up to 18 hours), the product of formula (VII) where X is C(OH)$CH_3$ may dehydrate to give the corresponding product where X is C=$CH_2$.

The alkenoic ester of formula (X) can be synthesised by reaction, at from about 20° to about 100° C., of the appropriate aldehyde or ketone of formula (XIII):

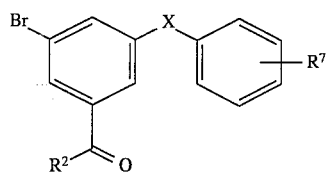

wherein $R^2$, and $R^7$ are as previously defined for formula (X), with a phosphonate of formula (XIV):

wherein $R^{12}$ is $C_1$–$C_4$ alkyl, preferably methyl or ethyl, and $R^1$ and $R^8$ are as defined for formula (X). The intermediate phosphorous ylid is generated in situ from (XIV) using a base such as sodium hydride in a suitable dry solvent, e.g. tetrahydrofuran, 1,2-dimethoxyethane or dimethylformamide.

Compounds of formula (XIII) wherein X is $CH_2$, CH(OH), C(OH)$CH_3$ or O, are obtainable from the corresponding dibromoarene precursors of formula (XV):

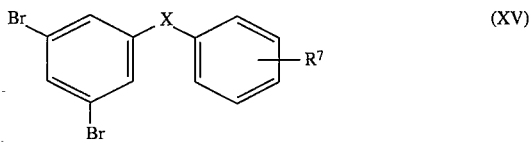

wherein $R^7$ is as previously defined for formula (XIII), as follows: (i) monobromo-lithium exchange using n-butyllithium in dry ether-hexane as solvent at about –70° C., and (ii) reaction of the resulting aryllithium with the appropriate tertiary amide, e.g. a N,N-dimethylamide of formula $R^2$CON(CH$_3$)$_2$, at from about –70° to about 0° C.

Compounds of formula (XV) may be derived from 1,3,5-tribromobenzene by one of several different procedures. For example, when X is $CH_2$, as follows: (i) monobromo-lithium exchange using n-butyllithium in dry ether-hexane at about –70° C., (ii) reaction of the resulting 3,5-dibromophenyllithium with an aromatic nitrile as required at from about –78° to about 0° C., and (iii) quenching and hydrolysis of the intermediate lithium-imine salt with hydrochloric acid at from about 0° to about 1000° C. These three steps afford the ketone precursors of (XV), i.e. compounds of formula (XV) wherein X is C=O, which are reduced under typical Wolff-Kishner (Huang-Minlon modification) conditions, using hydrazine hydrate followed by potassium hydroxide in refluxing ethylene glycol.

Alternatively, the ketone precursor may be formed by treatment of 3,5-dibromobemzonitrile with an aryllithium under the same conditions, followed by hydrolysis of the lithium imine salt.

When X is CH(OH) or C(OH)$CH_3$, compounds of formula (XV) may be synthesised by reaction of 3,5-dibromophenyllithium (prepared as indicated above) with either an aldehyde or ketone at from about –78° to about 0° C.

Alternatively, intermediates of formula (XV) where X is CH(OH) or C(OH)$CH_3$ may be synthesised by treatment of 3,5-dibromobenzaldehyde or 3,5-dibromoacetophenone with an aryllithium under the same conditions. An arylmagnesium halide may be used in place of the aryllithium, in which case the reaction may be carried out in diethyl ether, tetrahydrofuran or a mixture of the two at a temperature of 25° C. to the reflux temperature of the solvent.

Alternatively, compounds of formula (XIII) where X is CH(OH) or C(OH)$CH_3$ may be prepared in a "one pot" procedure from 3,5-dibromophenyllithium (prepared as indicated above) by reaction with either an aldehyde or ketone at about −70° C. After an appropriate time (15 minutes to 2 hours), addition of another equivalent of n-butyllithium followed by a N,N-dimethylamide gives the required aldehyde or ketone intermediate wherein $R^2$ is as previously defined. In a variant of this process, the order of addition may be varied such that the N,N-dimethylamide is added after the first lithiation step and the aldehyde or ketone is added after the second lithiation. Compounds of formula (XIII) wherein X is CO may also be prepared in a "one pot" procedure from 3,5-dibromophenyllithium by reaction with a N,N-dimethylamide at about −78° to −50° C. After an appropriate time (1–4 hours), addition of another equivalent of n-butyllithium followed by an aromatic nitrile, stirring at −78° to 0° C. for up to 4 hours, followed by quenching and hydrolysis of the intermediate affords the diketone of formula (XIII) wherein X is CO.

When X is O, compounds of formula (XV) are obtainable by reaction of 1,3,5-tribromobenzene with the anion of a phenol, generated using a base such as sodium hydride, in the presence of cuprous oxide in a suitable solvent, e.g. collidine, at about 200° C. Alternatively compounds where X is O may be obtained from the anion of 3,5-dibromophenol and a halobenzene derivative, wherein halo is preferably bromo.

Alternatively (XIII) may be converted to (VIIIa) by subjecting it to a Heck reaction with (XI) followed by Wittig-Horner reaction of the resulting acylarylalkenoate with (XIV).

Compounds of formula (VIIIb) may also be obtained by a variety of synthetic procedures, depending on the nature of X. For example, when X is $CH_2$, CH(OH), C(OH)$CH_3$, CO or O, and $R^1$, $R^2$ and $R^7$ are as previously defined for formula (VIIIb), they may be obtained from (XV) via a "double Heck reaction" using the required excess of alkenoate (XVI) under conditions previously described.

(XVI)

Compounds of formula (VIIIb) wherein $R^1$, $R^2$, $R^7$ and $R^8$ are as previously defined, and X is CH(OCOR$^{10}$) where $R^{10}$ is $C_1$–$C_4$ alkyl or phenyl may be prepared by treatment of the corresponding compound wherein X is CH(OH) with an acylating agent such as an acid anhydride of formula ($R^{10}$CO)$_2$O or acyl halide (preferably chloride) of formula $R^{10}$COhalo where halo and $R^{10}$ are as previously defined. These reactions are generally conducted in the presence of excess tertiary amine such as triethylamine, 4-dimethylaminopyridine (DMAP) or pyridine to act as acid scavenger, in a suitable solvent such as dichloromethane, at from about −75° to 40° C. Alternatively, pyridine can be used to act as both acid scavenger and solvent.

Compounds of formula (VII) wherein $R^1$, $R^2$, $R^3$, $R^4$, $R^7$ and $R^8$ are as previously defined, and X is CH(OCOR$^{10}$) where $R^{10}$ is $C_1$–$C_4$ alkyl or phenyl may be prepared by acylation of the corresponding compound where X is CH(OH) by methods analogous to those described above for the preparation of compounds of the formula (VIIIb).

Compounds of formula (VIIIc) may be obtained by procedures completely analogous to those described for the generation of (VIIIa) and (VIIIb), by employing the appropriate α,β-unsaturated nitrile for the Heck reaction or the appropriate cyanoalkylphosphonate for the Wittig-Horner reaction. These procedures are similarly applicable to compounds of formula (VIIIc) wherein $R^1$=$R^4$ and $R^2$=$R^3$.

Several of the possible functional group transformations involving the substituent $R^7$ and the linking group X described above for compounds of the formula I may also be carried out at intermediate stages, subject to compatability of the reaction conditions with other functional groups present in the intermediate. For example, oxidation of compound (IX), wherein X is CH(OH) and $R^1$, $R^2$, $R^7$ and $R^8$ are as previously defined, under Swern conditions gives the corresponding compound where X is CO.

The alkenoic esters of formulae (XI) and (XVI), the phosphonate of formulae (XIV), the α,β-unsaturated nitriles or cyanoalkylphosphonates required for compounds of formula (XIII), and the sulphonyl halides, acyl halides and acid anhydrides required in the previously described processes, when neither commercially available nor subseqently described, can be obtained by conventional synthetic procedures, in accordance with literature precedent, from readily accessible starting materials using appropriate reagents and reaction conditions.

Persons skilled in the art will recognise that the alkenes depicted hereinbefore may be obtained in alternative geometrically isomeric forms, or as mixtures of geometrical isomers, and are represented in one such form only in the interests of clarity and convenience.

Alternative biolabile esters to those hereinbefore defined by formula (II) may be obtained from the acids of formula (I) by standard reactions. For example, aryl and alkyl esters can be synthesised via activation of the carboxylic acid group of (I) in a variety of ways, such as by forming the acyl chloride, followed by reaction with the required phenol or alcohol. Alternatively, alkyl esters are obtainable by alkylation of a suitable alkali, or alkaline earth, metal carboxylate salt of a compound of formula (I).

The pharmaceutically acceptable salts of the compounds of formula (I) may also be prepared in a conventional manner. For example a solution of the free acid is treated with the appropriate base, either neat or in an appropriate solvent, and the resulting salt isolated either by filtration or by evaporation of the reaction solvent under reduced pressure.

All of the above reactions are entirely conventional and the necessary reagents and conditions for their performance can readily be established by reference to standard text books and to the Examples provided hereafter. Alternatives and variations will also be evident to persons skilled in the art to enable all the compounds defined by formula (I) to be prepared.

As previously mentioned, the compounds of the invention are able to antagonise the action of thromboxane $A_2$ and prostaglandin $H_2$ at the thromboxane $A_2$ receptor.

Thromboxane $A_2$ (TXA$_2$) is a naturally occurring prostanoid which is known to be a potent vasoconstrictor and platelet aggregating agent. TXA$_2$ is believed to be involved in a number of disease states including atherosclerosis, ischaemic heart disease, peripheral vascular disease and myocardial infarction. TXA$_2$ acts at the thromboxane $A_2$ receptor, at which site other prostanoids, notably prostaglandin $H_2$, may also be agonists.

TXA$_2$ synthetase inhibitors prevent formation of TXA$_2$ from the precursor PGH$_2$ which may be diverted to produce more of the vasodilator and antiaggregatory PGI$_2$. However, a possible drawback with this type of agent is that accumulated PGH$_2$ substrate can activate the TXA$_2$ receptor, thus partly eliminating or negating the benefit of suppressing TXA$_2$ formation. Furthermore, if inhibition of TXA$_2$ synthetase is incomplete, sufficient TXA$_2$ may be available to induce some platelet activation. Both of these drawbacks can be overcome if a TXA$_2$ receptor antagonist is present to block the action of any TXA$_2$ or accumulated PGH$_2$ substrate. It has been demonstrated that combination of a TXA$_2$ antagonist and a TXA$_2$ synthetase inhibitor produces a synergistic effect on platelet aggregation in vitro (Watts et al., *Brit. J. Pharmacol.*, 102, 497, 1991). In addition, administration of the TXA$_2$ antagonist sulotroban and the TXA2 synthetase inhibitor dazoxiben to human volunteers gave a stronger inhibition of platelet aggregation than either agent alone (Gresele et al, *J. Clin. Invest.*, 80, 1435, 1987).

Thus the compounds of the invention are of particular value when used in combination with a selective inhibitor of the thromboxane synthetase enzyme and the resulting combinations will find utility in the disease states already mentioned as well as those in which PGD$_2$ and PGF$_{2\alpha}$ may be implicated as mediators, such as diabetes, bronchial asthma, and other inflammatory conditions.

Thus the present invention also provides a pharmaceutical composition comprising as active ingredients a novel TXA$_2$ receptor antagonist of the formula (I) as hereinbefore defined and a TXA$_2$ synthetase inhibitor, together with a pharmaceutically acceptable diluent or carrier.

Suitable TXA$_2$ synthetase inhibitors for inclusion as active ingredients in the composition according to the invention include, for example, the known compounds-:

1) 4-[2-(1H-imidazol-1-yl)ethoxy]benzoic acid, (dazoxiben, R. P. Dickinson, et al, *J. Med. Chem.*, 1985, 28, 1427–1432),
2) 3-(1H-imidazol-1-ylmethyl)-2-methyl-1H-indole-1-propanoic acid, (dazmegrel, R. P. Dickinson, et al, *J. Med. Chem.*, 1986, 29, 342–346),
3) 2-methyl-3-(3-pyridylmethyl)-1H-indole-1-propanoic acid, (European patent 0054417),
4) 3-methyl-2-(3-pyridylmethyl)benzo[b]thiophene-5-carboxylic acid, (UK-49,883, P. E. Cross, R. P. Dickinson, *Spec Publ. Royal Soc. Chem.* No 50, p 268–285, 1984),
5) 1,3-dimethyl-2-(1H-imidazol-1-ylmethyl)-1H-indol-5-carboxylic acid, (R. P. Dickinson et al, *J. Med. Chem.*, 1986, 29, 1643–1650),
6) a carboxy, lower alkoxycarbonyl or carbamoyl substituted benzothiophene, benzofuran or indole as claimed in European patent 0073663, or the novel compound-:
7) 2-methyl-3-(3-pyridyl)-1H-indole-1-pentanoic acid; or any other thromboxane synthetase inhibitor which acts in a synergistic manner and is chemically compatible with the novel compounds of formula (I).

The biological activity of the compounds of the invention can be demonstrated using the following in vitro and in vivo assay procedures.

1. Thromboxane A$_2$ receptor antagonism

Spirally cut rat aortic strips, mounted for isometric tension recording in 20 ml organ baths, are bathed in Krebs-bicarbonate solution at 37° C. Following an incubation period of 2 hours under 1 gram resting tension, the tissues are pre-treated with U-46619 (a thromboxane A$_2$ receptor agonist) for 10 minutes, then washed and the tissues allowed to equilibriate for a further 1 hour. Cumulative doses of U-46619 over the range 1nM-100nM are sequentially included in the bathing fluid and increases in the tissue tension noted.

The test compounds are incubated with the tissue for 15 minutes prior to repeating the cumulative dosing of U-46619 and the ability of the compound to antagonize the thromboxane A$_2$ receptor is determined from the dose-response curves for U-46619 in the presence of varied concentrations of the test compound.

2. Anaesthetised Rabbits

Thromboxane A$_2$ receptor antagonism is evaluated ex vivo in anaesthetised rabbits as follows:

New Zealand White rabbits (2–2.5 kg) are anaesthetised with fentanyl citrate (0.189 mg) and fluanisone (6 mg) intramuscularly and midazolam (3 mg) intravenously and maintained by an intravenous infusion of fentanyl citrate (0,315 mg), fluanisone (1 mg) and midazolam (1 mg) per hour. After cannulation of the trachea, a carotid artery is cannulated for collection of blood samples. The catheter is kept patent by the presence within the catheter of saline containing heparin (50 µ/ml). Control carotid arterial blood samples are taken 25 and 5 minutes prior to administration of the test compound via a marginal ear vein. Two groups of rabbits are used. The first group receives 0.01 mg/kg of the test compound followed, at ten minute intervals, by 0.03, 0.1, 0.3, 1.0, 3.0 and 10 mg/kg doses; the second group comprises the controls. Carotid arterial blood samples are taken 5 minutes after all doses. At each time point, a 900 µl blood sample is immediately mixed with 100 µl of trisodium citrate (3.15%). After 90 minutes incubation at room temperature, this sample is mixed in equal proportions with an aggregometry buffer (J. Pharmacol. Methods, 1981, 6, 315) and brought to 37° C. Electrodes for the measurement of electrical impedance are placed in the blood and U-46619 (final concentration 3 µM) is added to the blood. Antagonism of platelet thromboxane A$_2$ receptors by the compound is assessed by comparing the change in electrical impedance produced by U-46619 in compound-treated rabbits with the untreated controls.

3. Conscious Dogs

Thromboxane A$_2$ receptor antagonism may also be evaluated ex vivo in sling-restrained conscious dogs after oral (p.o.) or intravenous (i.v.) administration of a compound of the invention. The sampling and assaying procedures employed are similar to those described for the ex vivo anaesthetised rabbit experiments.

For administration to man, in the therapy or prevention of diseases or adverse medical conditions in which TXA$_2$ is implicated as a causative agent, oral dosages of the compounds would be expected to be in the range of from 2–200 mg daily for an average adult patient (70 kg). Thus for a typical adult patient, individual tablets or capsules contain from 1 to 200 mg of active compound, in a suitable pharmaceutically acceptable vehicle or carrier, for administration as a single dose, or in multiple doses, once or several times a day. Dosages for intravenous administration would typically be within the range of from 1 to 200 mg per single dose required. In practice the physician will determine the actual dosage which will be most suitable for an individual patient and it will vary with the age, weight and response of the particular patient, and with the condition being treated. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example enough salts or glucose, to make the solution isotonic with blood.

Thus the invention provides a pharmaceutical composition comprising a compound of formula (I), or a pharmaceutically acceptable salt or biolabile ester thereof, together with a pharmaceutically acceptable diluent or carrier.

The invention also provides a compound of formula (I), or a pharmaceutically acceptable salt or biolabile ester thereof, or a pharmaceutical composition containing any of these entities, for use in medicine.

The invention further includes the use of a compound of formula (I), or a pharmaceutically acceptable salt or a biolabile ester thereof, for the manufacture of a medicament for the treatment of disease conditions in which thromboxane $A_2$ is a causative agent.

In a further aspect, the invention provides a method of treating or preventing disease conditions in which thromboxane $A_2$ is a causative agent in a mammal (including a human being) which comprises administering to said mammal a therapeutically effective amount of a compound of formula (I), or a pharmaceutically acceptable salt, or a biolabile ester thereof.

The invention also includes any novel intermediates disclosed herein such as those of formulae (II), (III), and (IV). The synthesis of the compounds of the invention and of the intermediates for use in their preparation are illustrated by the following Examples and Preparations. The purity of the compounds was routinely monitored by thin layer chromatography (TLC) using Merck Kieselgel 60 $F_{254}$ plates and the following solvent systems (SS):

SS1. Dichloromethane/hexane (1:1)
SS2. Hexane
SS3. Dichloromethane
SS4. Dichloromethane/methanol (95:5)
SS5. Dichloromethane/methanol/0.880 ammonia (90:10:1)
SS6. Ethyl acetate/hexane (1:5)
SS7. Etyl acetate/hexane (1:1)
SS8. Dichloromethane/methanol (9:1)
SS9. Dichloromethane/methanol/acetic acid (100:5:0.5)
SS10. Ethyl acetate/hexane/acetic acid (10:10:1)
SS11. Dichloromethane/methanol/acetic acid (90:10:1)
SS12. Ethyl acetate/hexane (5:1)
SS13. Dichloromethane/ethanol (20:1)
SS14. Ethyl acetate/hexane/acetic acid (50:50:1)
SS15. Ethyl acetate/hexane/acetic acid (70:30:1)

$^1$H-Nuclear magnetic resonance (NMR) spectra were recorded using either a Nicolet QE-300 or a Bruker AC-300 spectrometer and were in all cases consistent with the proposed structures. Chemical shifts are given in parts-per-million downfield from tetramethylsilane using conventional abbreviations for designation of major peaks: s, singlet; d, doublet; t, triplet; m, multiplet and br, broad.

PREPARATION 1

3,5-Dibromo-α-(4-fluorophenyl)benzenemethanol

A 2.5M solution of n-butyllithium in hexane (44.0 ml) was added dropwise to a stirred suspension of 1,3,5-tribromobenzene (31.5 g) in dry ether (1000 ml) at −78° C. under an atmosphere of dry nitrogen. The resulting mixture was stirred at this temperature for 30 minutes and the 4-fluorobenzaldehyde (13.65 g) was added dropwise. Stirring at −78° C. was continued for a further 30 minutes and then the reaction was quenched by the addition of water. The temperature was allowed to reach room temperature and the organic layer was separated and dried ($MgSO_4$). Evaporation of the solvent gave an oil which was chromatographed on silica gel. The column was eluted with dichloromethane/hexane (1:5), gradually increasing the ratio of solvents to 2:3. The product fractions were combined, evaporated and the residue was triturated with hexane to give the title compound (31.42 g), m.p. 92°–93° C. Found: C,43.75; H,2.43. $C_{13}H_9Br_2OF$ requires C,43.37; H,2.52%.

The following compounds were prepared similarly from the appropriate aldehyde or ketone: 3,5-Dibromo-α-(2-fluorophenyl)benzenemethanol (obtained as an oil), Rf 0.2 (SS 1). δ($CDCl_3$): 2.40(1H,br,s), 6.08(1H,s),7.03–7.09(1H,m), 7.16–7.22(1H,m), 7.27–7.33(1H,m), 7.42–7.48(1H,m), 7.50(2H,d), 7.58(1H,d). 3,5-Dibromo-α-(4-fluorophenyl)-α-methylbenzenemethanol,m.p. 72°–73° C. Found: C,44.95; H,2.90. $C_{14}H_{11}Br_2FO$ requires C,44.95; H,2.96%.

PREPARATION 2

3,5-Dibromo-α-(2-methoxyphenyl)benzenemethanol

1-Bromo-2-methoxybenzene (7.48 g) was dissolved in dry diethyl ether (50 ml) and a 5 ml aliquot of the solution was removed and added to a mixture of magnesium turnings (1.0 g) and a crystal of iodine. The mixture was heated to reflux to initiate reaction and the heating source was removed. The remaining bromomethoxybenzene solution was then added at a sufficient rate to maintain reflux, and the mixture was heated under reflux for a further 1 hour. It was then cooled slightly and a solution of 3,5-dibromobenzaldehyde (10.0 g) in dry tetrahydrofuran (40 ml) was added dropwise. The mixture was heated under reflux for 30 minutes, then cooled to room temperature and a solution of ammonium chloride (8.0 g) in water (40 ml) was added with rapid stirring. The mixture was diluted with ether and the organic phase was separated, washed with water and dried ($MgSO_4$). The solvent was evaporated and the residue was chromatographed on silica gel. Elution was commenced with hexane/dichloromethane (5:1), and the proportion of dichloromethane was gradually increased to give a ratio of 1:4. The later fractions containing product were combined and evaporated to give the title compound (11.85 g), m.p. 112°–116° C. (from cyclohexane). Found: C,45.52; H,3.09. $C_{14}H_{12}Br_2O_2$ requires C,45.19; H,3.25%.

PREPARATION 3

1,3-Dibromo-5-(4-fluorophenoxy)benzene

Sodium hydride (3.24 g of 60% suspension in mineral oil was added portionwise to a stirred mixture of 1,3,5-tribromobenzene (76.4 g), 4-fluorophenol (18.16 g), and cuprous oxide (11.6 g) in collidine (400 ml) at room temperature. When evolution of hydrogen had ceased the mixture was heated under reflux with stirring for 8 hours. It was then cooled and filtered. The residue was washed with ethyl acetate followed by concentrated aqueous ammonia, and the combined filtrate and washings were partitioned between ethyl acetate and water. The organic layer was washed twice with brine and evaporated. The residue was dissolved in ethyl acetate, and the solution was filtered, washed several times with citric acid solution and dried ($MgSO_4$). The solvent was evaporated, and the residue was dissolved in hot hexane. The solution was filtered and the filtrate was evaporated. The residue was chromatographed on silica using hexane as eluent to give the title compound as an oil (18.21 g), Rf 0.31(SS 2). Found: C,41.71; H,1.97. $C_{12}H_7Br_2FO$ requires C,41.66; H,2.04%.

PREPARATION 4

3-Bromo-5-[(4-fluorophenyl)hydroxymethyl]benzaldehyde

A 2.5M solution of n-butyllithium in hexane (22.0 ml) was added dropwise to a stirred suspension of 1,3,5-tribromobenzene (15.74 g) in dry diethyl ether (500 ml) at −78° C. under an atmosphere of dry nitrogen. The resulting mixture was stirred at this temperature for 30 minutes and then 4-fluorobenzaldehyde (6.83 g) was added dropwise. Stirring at −78° C. was continued for a further 30 minutes and then another equivalent of n-butyllithium (22.0 ml of 2.5M solution in hexane) was added dropwise. The mixture was stirred at −78° C. for another 15 minutes and then N,N-dimethylformamide (15.45 g) was added. Stirring was continued for 1 hour and then water (200 ml) was added. The mixture was allowed to reach room temperature and the organic layer was separated and dried (MgSO$_4$). Evaporation of the solvent gave an oil which was chromatographed on silica gel. Elution with dichloromethane gave impurity, and further elution with dichloromethane/methanol (99:1) gave the title compound as a gum (10.94 g), Rf 0.2 (SS 3). Found: C,53.99; H,3.41. $C_{14}H_{10}BrFO_2$ requires C,54.39; H,3.26%

The following compounds were prepared similarly using the appropriate aldehyde-:

3-Bromo-5-[hydroxy(phenyl)methyl]benzaldehyde, Rf 0.2 (SS 3). δ(CDCl$_3$): 2.43(1H,s), 5.89(1H,s), 7.32–7.38(5H,m), 7.83(2H,m), 7.90(1H,m), 9.91(1H, s). 3-Bromo-5-[(3-fluorophenyl)hydroxymethyl]benzaldehyde, Rf 0.15 (SS 3). δ(CDCl$_3$): 2.62(1H,br,s), 5.86(1H,s), 6.98–7.15(3H,m), 7.31–7.38(1H,m), 7.80(2H,m), 7.91(1H,m), 9.91(1H,s).

PREPARATION 5

3-Bromo-5-[1-(4-fluorophenyl)-1-hydroxyethyl]-benzaldehyde

A 2.5M solution of n-butyllithium in hexane (10.7 ml) was added dropwise to a stirred suspension of 3,5-dibromo-α-(4-fluorophenyl)-α-methylbenzenemethanol (5.90 g) in dry diethyl ether (160 ml) at −78° C. under an atmosphere of dry nitrogen. The resulting mixture was stirred at this temperature for 30 minutes and then N,N-dimethylformamide (2.93 g) was added dropwise. Stirring at −78° C. was continued for 1 hour and then the reaction was quenched by the addition of water. The temperature was allowed to reach room temperature and the organic layer was separated, washed with water and dried (MgSO$_4$). Evaporation of the solvent gave an oil which was chromatographed on silica gel. Elution was commenced with hexane/dichloromethane (1:1), and the ratio was gradually changed to hexane/dichloromethane (1:5). The later product fractions were combined and evaporated to give the title compound as an oil (2.10 g), Rf 0.15 (SS 1). Found: C,55.39; H,3.78. $C_{15}H_{12}BrO_2F$ requires C,55.75; H,3.74%.

PREPARATION 6

Ethyl 3-[3-bromo-5-[(4-fluorophenyl)hydroxymethyl]-phenyl]-2-propenoate

Triethylphosphonoacetate (8.30 g) was added dropwise to a stirred, ice-cooled suspension of sodium hydride (1.48 g of 60% suspension in mineral oil) in dry tetrahydrofuran (50 ml), and the mixture was stirred for 30 minutes to give a clear solution. A solution of 3-bromo-5-[(4-fluorophenyl)hydroxymethyl)]-benzaldehyde (10.38 g) in dry tetrahydrofuran (50 ml) was added dropwise. The solution was stirred at 0° C. for 1 hour and then poured into a mixture of ether and water. The aqueous layer was separated, extracted with ether, and the organic layers were combined, washed with water and dried (MgSO$_4$). The solvent was evaporated and the residue was chromatographed on silica gel using dichloromethane as eluent. The product fractions were combined and evaporated, and the residue was crystallised from ether/hexane to give the title compound (10.22 g), m.p. 82°–84° C. Found: C,57.35; H,4.04. $C_{18}H_{16}BrFO_3$ requires C,57.01; H,4.25%.

The following compounds were prepared similarly from the appropriate aldehyde-:

Ethyl 3-[3-bromo-5-[hydroxy(phenyl)methyl]phenyl]-2-propenoate, m.p. 104°–105° C. Found: C,60.04; H,4.62. $C_{18}H_{17}BrO_3$ requires: C,59.85; H,4.74%. Ethyl-3-[3-bromo-5-[(3-fluorophenyl)hydroxymethyl)]-phenyl]-2-propenoate, m.p. 86°–87° C. Found: C,57.04; H,4.26. $C_{18}H_{16}BrFO_3$ requires: C,57.01; H,4.25% Ethyl-3-[3-bromo-5-[1-(4-fluorophenyl)-1-hydroxyethyl]phenyl]-2-propenoate, m.p. 97°–98° C. Found: C,57.58; H,4.56. $C_{19}H_{18}BrFO_3$ requires: C,58.03; H,4.61%

PREPARATION 7

Ethyl 3-[3-(2-carbamoylethenyl)-5-[(4-fluorophenyl)-hydroxymethyl]phenyl]2-propenoate A mixture of ethyl 3-[3-bromo-5-[(4-fluorophenyl)hydroxymethyl]phenyl]-2-propenoate (9.50 g), acrylamide (2.67 g), palladium(II) acetate (0.306 g), tri-o-tolylphosphine (0.763 g) and triethylamine (3.80 g) in acetonitrile (10 ml) was heated to 100° C. for 4 hours under an atmosphere of nitrogen and then cooled. Water (150 ml) and dichloromethane (150 ml) was added and the mixture was warmed with stirring to disperse the solid residue. The mixture was cooled and filtered, and the solid was dissolved in hot isopropanol (500 ml). The solution was filtered hot using a filter aid, and the filtrate was concentrated until crystallisation commenced. An equal volume of ether was added and the mixture was allowed to cool. The solid was filtered off and dried to give the title compound (5.50 g), m.p. 197°–199° C. Found: C,68.55; H,5.17; N,4.01. $C_{21}H_{20}FNO_4$ requires C,68.28; H,5.46; N,3.79%.

Drying (MgSO$_4$) and evaporation of the dichloromethane solution followed-by crystallisation of the residue from isopropanol/ether gave an additional 2.21 g of product, m.p. 196°–198° C.

The following compounds were prepared similarly:

Ethyl 3-[3-(2-carbamoylethenyl)-5-[hydroxy(phenyl)methyl]phenyl]-2-propenoate, m.p. 179°–180° C. Found: C,71.26; H,6.36; N,3.92. $C_{21}H_{22}NO_4$ requires: C,71.57; H,6.29; N3.97%.

Ethyl 3-[3-(2-carbamoylethenyl)-5-[(3-fluorophenyl)hydroxymethyl]phenyl]-2-propenoate, m.p. 166°–168° C. Found: C,67.49; H,5.43; N,3.77. $C_{21}H_{21}FNO_4$ requires: C,68.10; H,5.71; N,3.78%.

Ethyl 3-[3-(2-carbamoylethenyl)-5-[1-(4-fluorophenyl)ethenyl]phenyl]-2-propenoate, obtained using ethyl 3-[3-bromo-5-[1-(4-fluorophenyl)hydroxyethyl]phenyl]-2propenoate as starting material, reaction time 18 hours, gum, Rf 0.3(SS 4). δ (CDCl$_3$): 1.35(3H,t), 4.27(2H,q), 5.47(1H,s), 5.52(1H,s), 5.63(2H,br), 6.43(1H,d), 6.50(1H,d), 7.02–7.08(2H,m), 7.27–7.33(2H,m), 7.46(2H,s), 7.61–7.65(3H,m), 7.69(1H,d).

PREPARATION 8

Diethyl 3,3'-[5-(4-fluorophenyl)hydrozymethyl-1,3-phenylene]bis-2-propenoate A mixture of 3,5-dibromo-α-(4-fluorophenyl)benzenemethanol (13.8 g), ethyl acrylate (11.5 g), palladium(II) acetate (469 mg), tri-o-tolylphosphine (1.17 g), triethylamine (16 ml) and acetonitrile (25 ml) was heated under reflux under an atmosphere of dry nitrogen for 4 hours. The mixture was cooled and partitioned between ether and water. The aqueous layer was extracted several times with ether, and the combined organic layers were washed with water and dried (MgSO$_4$). Evaporation of the solvent gave an oil which was chromatographed on silica gel. Elution with dichloromethane first gave impurity followed by pure product. The product fractions were combined and evaporated to give the title compound (9.32 g), m.p. 98°–100° C. Found: C,69.40; H,5.85. $C_{23}H_{23}FO_5$ requires C,69.33; H,5.82%.

The following compounds were prepared similarly-:

Diethyl 3,3'-[5-(2-fluorophenyl)hydroxymethyl-1,3-phenylene]bis-2-propenoate, m.p. 102°–103° C. Found: C,69.45; H,5.83. $C_{23}H_{23}FO_5$ requires C,69.33; H,5.82% Diethyl 3,3'[5-(2-methoxyphenyl)hydroxymethyl-1,3-phenylene]bis-2-propenoate, m.p. 104°–107° C. Found: C,70.36; H,6.46. $C_{24}H_{26}O_6$ requires C,70.23; H,6.39% Diethyl 3,3'-[5-(4-fluorophenoxy)1,3-phenylene]bis-2-propenoate, oil, Rf 0.25 (SS 3). Found: C,68.47; H,5.40. $C_{22}H_{21}FO_5$ requires C,68.74; H,5.06%.

PREPARATION 9

Diethyl 3,3'-[5-[α-acetoxy-(4-fluorophenyl)methyl]-1,3-phenylene]bis-2-propenoate A solution of diethyl 3,3'-[5-(4-fluorophenyl)-hydroxymethyl-1,3-phenylene]bis-2-propenoate (9.30 g), acetic anhydride (4.40 ml), pyridine (50 ml) and 4-dimethylaminopyridine (50 mg) in dichloromethane (50 ml) was stirred at room temperature for 2 hours. The solution was then washed successively with water, 1N hydrochloric acid and sodium bicarbonate solution, and then dried (MgSO$_4$). Evaporation of the solvent gave an oil which was triturated with ether to induce crystallisation. The mixture was diluted with hexane and filtered to give the title compound (9.50 g), m.p. 123°–125° C. Found: C,68.47; H,5.79. $C_{25}H_{25}FO_6$ requires C,68.17; H,5.72%.

The following compounds were prepared similarly-:

Diethyl 3,3'- [5-[α-acetoxy- (2-fluorophenyl) methyl]-1,3-phenylene]bis-2-propenoate, m.p. 83°–85° C. Found: C,68.15; H,5.42. $C_{25}H_{25}FO_6$ requires C,68.17; H,5.72% Diethyl 3,3'-[5-[α-acetoxy-(2-methoxyphenyl)methyl]-1,3-phenylene]bis-2-propenoate, m.p. 128°–132° C. Found: C,69.22; H,6.38. $C_{26}H_{28}O_7$ requires C,69.01; H,6.24%

PREPARATION 10

Ethyl 3-[3-[α-acetoxy-(phenylmethyl)]-5-[(2-carbamoyl)ethenyl]phenyl]-2-propenoate A mixture of ethyl 3-[3-(2-carbamoyl)ethenyl-5-[hydroxy(phenyl)methyl]phenyl]-2-propenoate (4.46 g), acetic anhydride (3.12 g), 4-dimethylamino-pyridine (30 mg) and pyridine was stirred at room temperature for 18 hours. The resulting solution was diluted with ethyl acetate and washed twice with water, twice with 1N hydrochloric acid and twice with sodium bicarbonate solution. It was dried (MgSO$_4$) and evaporated, and the gummy residue was dissolved in a small volume of ether. An equal volume of hexane was added and the mixture was kept at 0° C. for 18 hours. The solid was filtered off and dried to give the title compound (3.98 g), m.p. 101°–102° C. Found: C,70.29; H,6.00; N,3.48. $C_{23}H_{23}NO_5F$ requires C,70.21; H,5.89; N,3.56%

The following compounds were prepared similarly-:

Ethyl 3-[3-[α-acetoxy-(4-fluorophenyl)methyl]-5-(2-carbamoylethenyl)phenyl]-2-propenoate, m.p. 89°–91° C. Found: C,67.09; H,5.21; N,3.15. $C_{23}H_{22}FNO_5$ requires: C,67.14; H,5.39; N,3.41%

Ethyl 3-[3-[α-acetoxy-(3-fluorophenyl)methyl]-5-(2-carbamoylethenyl)phenyl]-2-propenoate, m.p. 161°–162° C. Found: C,66.55; H,5.45; N,3.18. $C_{23}H_{22}FNO_5$ requires C,67.14; H,5.39; N,3.41%.

PREPARATION 11

Diethyl 5-[(4-fluorophenyl)methyl],1,3-benzenedipropanoate

A mixture of diethyl 3,3'-[5-[α-acetoxy-(4-fluorophenyl)methyl]-1,3-phenylene]bis-2-propenoate (9.20 g) and 10% palladium/carbon (1.0 g) in ethyl acetate (100 ml) was hydrogenated at 50 p.s.i. (3.45 bar) and room temperature for 6 hours. The mixture was filtered and the filtrate was washed with sodium bicarbonate solution and dried (MgSO$_4$). Evaporation of the solvent gave the title compound as a gum (8.07 g); Rf 0.5 (SS 3). Found: C,72.22; H,6.95. $C_{23}H_{27}FO_4$ requires C,71.48; H,7.04%.

The following compounds were prepared similarly-:

Diethyl 5-[(2-fluorophenyl)methyl]-1,3-benzenedipropanoate, oil, Rf 0.8 (SS 5), δ(CDCl$_3$): 1.23(6H,t), 2.57(4H,t), 2.89(4H,t), 3.93(2H,s), 4.11(4H,q), 6.89(3H,s), 4.01–4.20(4H,m).

Diethyl 5-[(2-methoxyphenyl)methyl]-1,3-benzenedipropanoate, oil, Rf 0.3 (SS 6), Found: C,72.15; H,7.67. $C_{24}H_{30}O_5$ requires C,72.33; H,7.59%.

PREPARATION 12

Diethyl 5-[(4-fluorophenyl)hydroxymethyl]-1,3-benzenedipropanoate

A mixture of diethyl 3,3'-[5-(4-fluorophenyl)-hydroxymethyl-1,3-phenylene]bis-2-propenoate (30.6 g), ammonium formate (48.0 g) and 10% palladium on carbon (3.0 g) in ethanol (250 ml) and tetrahydrofuran (250 ml) was heated at 60° C. for 1.5 hours, and then cooled. The mixture was filtered and the residue was washed with ethanol. The combined filtrate and washings were evaporated, and the

PREPARATION 13

Diethyl 5-(4-fluorophenoxy)-1,3-benzenedipropanoate

Treatment of diethyl 3,3'-[5-(4-fluorophenoxy)-1,3-phenylene]bis-2-propenoate (17.0 g) with ammonium formate (27.85 g) and 10% of palladium on carbon (1.70 g) according to the method of Preparation 12 gave the title compound as an oil (12.12 g), Rf 0.30 (SS 1). Found: C,68.01; H,6.46. $C_{22}H_{25}FO5$ requires C,68.03; H,6.49%.

PREPARATION 14

Diethyl 5-(4-fluorobenzoyl)-1,3-benzenedipropanoate

Dimethylsulphoxide (16.2 ml) was added dropwise to a stirred solution of oxalyl chloride (11.55 g) in dry dichloromethane (500 ml) at −78° C. under an atmosphere of dry nitrogen. The mixture was stirred for 10 minutes and then a solution of diethyl 5-[(4-fluorophenyl)hydroxymethyl]-1,3-benzenedipropanoate (30.65 g) in dry dichloromethane (150 ml) was added dropwise. The mixture was stirred at −78° C. for 30 minutes, triethylamine (23.03 g) was added, and stirring was continued for a further 10 minutes. The temperature was allowed to rise to room temperature, and the mixture was washed with water. The organic layer was separated, dried (MgSO$_4$) and evaporated. The residue was chromatographed on silica gel. Elution with dichloromethane followed by dichloromethane/methanol (50:1) gave the title compound as an oil (28.92 g), Rf 0.75 (SS 4). Found: C,69.08; H,6.46. $C_{23}H_{25}FO_5$ requires: C,68.98; H,6.29%.

PREPARATION 15

Monoethyl 5-[(4-fluorophenyl)methyl]-1,3-benzenedipropanoate

2N Sodium hydroxide solution (10 ml) was added to a stirred solution of diethyl 5-[(4-fluorophenyl)methyl]-1,3-benzenedipropanoate (7.70 g) in ethanol (50 ml) and the mixture was allowed to stand for 2 hours and then evaporated. The residue was partitioned between ether and water. The ether layer was separated, dried (MgSO$_4$) and evaporated to give starting material (3.35 g). The aqueous layer was acidified with 2N hydrochloric acid and the mixture was extracted several times with ethyl acetate. The combined extracts were dried (MgSO$_4$) and evaporated, and the residue was chromatographed on silica gel. The column was eluted with ethyl acetate/hexane (1:1), gradually increasing the polarity of the eluent to pure ethyl acetate. The product fractions were combined and evaporated to give the title compound as gum (3.12 g), Rf 0.5 (SS 7) Found: C,70.17; H,6.60. $C_{21}H_{23}FO_4$ requires C,70.37; H,6.47%.

The following compounds were prepared similarly-:

Monoethyl 5-[2-fluorophenyl)methyl]-1,3-benzenedipropanoate, oil, Rf 0.65 (SS 8); δ(CDCl$_3$):1.22(3H,t), 2.60(2H,t),2.68(2H,t),2.90(4H,m),3.95(2H,s),4.14(2H, q), 6.30(3H,brs) 7.0–7.25(4H,m), 11.0(1H,br,s).

Monoethyl 5-[(2-methoxyphenyl)methyl]-1,3-benzenedipropanoate, oil, Rf 0.30 (SS 9). Found: C,70.84; H,6.85. $C_{22}H_{26}O_5$ requires: C,71.33; H,7.00%

Monoethyl 5-(4-fluorobenzoyl)-1,3-dipropanoate, oil, Rf 0.25 (SS 8). Found: C,67.47; H,5.76. $C_{21}H_{21}FO_5$ requires C,67.73; H,5.68%.

Monoethyl-5-(4-fluorophenoxy)-1,3-dipropanoate, oil, Rf 0.4 (SS 10). Found: C,66.69; H,6.22 requires C,66.66; H,5.87%.

PREPARATION 16

Ethyl 3-(2-carbamoylethyl)-5-[(4-fluorophenyl)methyl]-benzenepropanoate

Oxalyl chloride (17.8 g) followed by N,N-dimethylformamide (5 drops) were added to a stirred solution of monoethyl 5-[(4-fluorophenyl)methyl]-1,3-benzenedipropanoate (45.8 g) in dry dichloromethane (200 ml) at room temperature. The solution was stirred at room temperature for 3 hours and then evaporated. The residue was dissolved in diethyl ether (150 ml) and the solution was added slowly to a vigorously stirred mixture of concentrated aqueous ammonia (500 ml) and diethyl ether (200 ml). The mixture was stirred for 3 hours, and the aqueous layer was separated and extracted twice with diethyl ether (300 ml) and once with ethyl acetate (200 ml). The organic layers were combined, dried (MgSO$_4$), evaporated, and the residue was crystallised from ether/hexane to give the title compound (42.5 g), m.p. 69°–70° C. Found: C,70.05; H,7.13; N,4.02. $C_{21}H_{24}FNO_3$ requires C,70.57; H,6.77; N,3.92%.

The following compounds were prepared similarly from the corresponding acids-:

Ethyl 3-(2-carbamoylethyl)-5-[(2-fluorophenyl)methyl]-benzene propanoate, oil, Rf 0.55 (SS 11), δ(CDCl$_3$): 1.11(3H,t), 2.48(2H,t), 2.57(2H,t), 2.85–2.93(4H,m), 3.95(2H,s), 4.11(2H,q), 5.40(2H,br,d), 6.91(3H,s), 7.00–7.25(4H,m).

Ethyl 3-(2-Carbamoylethyl-5-[(2-methoxyphenyl)methyl]benzene propanoate, m.p.70°–75° C. Found: C,71.23; H,7.40; N,3.63. $C_{22}H_{27}NO_4$ requires C,71.52; H,7.37; N,3.79%

Ethyl 3-(2-carbamoylethyl)-5-(4-fluorobenzoyl)benzene propanoate, m.p. 96°–98° C., Found: C,68.06; H,5.89; N,3.68. $C_{21}H_{22}FNO_4$ requires C,67.91; H,5.97; N,3.77% Ethyl 3-(2-carbamoylethyl)-5-(4-fluorophenoxy)benzene propanoate, m.p. 74°–75° C. Found: C,67.06; H,6.32; N, 3.95. $C_{20}H_{22}FNO_4$ requires C, 66.84; H, 6.17; N, 3.90%.

PREPARATION 17

Ethyl 3-(2-carbamoylethy1)-5-[4-fluorophenyl)methyl]benzenepropanoate

A solution of ethyl 3-[3-[α-acetoxy-(4-fluorophenyl)methyl]-5-[(2-carbamoyl)ethenyl]phenyl]-2-propenoate (7.50 g) in ethyl acetate (75 ml) was hydrogenated for 5 hours at room temperature and 3.5 atmospheres in the presence of 10% palladium on carbon (0.70 g). The mixture was filtered using a filter aid and the residue was washed with ethyl acetate. The filtrate and washings were combined, washed with sodium carbonate solution and dried (MgSO$_4$). The solvent was evaporated and the residue was triturated with hexane to give the title compound (6.05 g), m.p 68°–70° C. identical to the product of Preparation 16.

The following compounds were prepared similarly-:

Ethyl 3-(2-carbamoylethyl)-5-(phenylmethyl)benzene propanoate, oil, Rf 0.35 (SS 12), δ(CDCl$_3$): 1.11(3H,t), 2.48(2H,t), 2.57(2H,t), 2.87–2.93(4H,m), 3.92(2H,s), 4.09(2H,q), 5.35(2H,br,s), 6.89(3H,s), 7.15–7.30(5H, m).

Ethyl 3-(2-carbamoylethyl)-5-(3-fluorophenylmethyl)-benzene propanoate, m.p. 66°–67° C. Found: C,70.84; H,6.97; N,3.62. C$_{21}$H$_{24}$FNO$_3$ requires C,70.57; H,6.77; N,3.92%.

Ethyl 3-(2-carbamoylethyl-5-[1-(4-fluorophenyl)ethyl] benzene propanoate, (using ethyl 3-[3-[(2-carbamoyl)ethenyl]-5-[1-(4-fluorophenyl)ethenyl]phenyl]-2-propenoate as starting material), oil, δ(CDCl$_3$): 1.11(3H,t), 1.59(3H,d), 2.48(2H,t), 2.57 (2H,t), 2.84–2.92(4H,m), 4.08(2H,q), ca 4.05(1H,q), 5.46(1H, br,s), 6.70(1H,br,s), 6.90–7.0(5H,m), 7.12–7.17 (2H, m).

PREPARATION 18

Ethyl 3-[2-(t-butoxycarbonylamino)ethyl]-5-[(4-fluorophenyl)methyl]benzenepropanoate A solution of monoethyl 5-[(4-fluorophenyl)-methyl]-1,3-benzenedipropanoate (3.0 g), diphenyl-phosphoryl azide (2.51 g) and triethylamine (1.3 ml) in dry t-butanol (25 ml) was stirred at room temperature for 15 minutes and then heated under reflux for 20 hours. The solution was evaporated and the residue was partitioned between ether and wateT. The ether layer was separated, dried (MgSO$_4$) and evaporated to give an oil which was chromatographed on silica gel. Elution with dichloromethane gave the title compound as a gum (2.41 g), Rf 0.2(SS 3). N.M.R. δ(CDCl$_3$): 1.23(3H,t), 1.44(9H,s), 2.58(2H,t), 2.72(2H,t), 2.88(2H,t), 3.32(2H,m), 3.89(2H,s), 4.10(2H,q), 4.50(1H,br), 6.82–6.90(3H), 6.94–7.0(2H,m), 7.09–7.15(2H,m).

PREPARATION 19

Ethyl 3-(2-aminoethyl)-5-[(4-fluorophenyl)methyl]-benzenepropanoate

A solution of ethyl 3-[2-(t-butoxycarbonylamino)ethyl]-5-[(4-fluorophenyl)methyl]benzene-propanoate (2.36 g) and trifluoroacetic acid (5 ml) in dichloromethane (25 ml) was allowed to stand at room temperature overnight and then evaporated. The residue was partitioned between ether and dilute sodium hydroxide solution. The organic layer was separated, washed with water and dried (MgSO$_4$). The solvent was evaporated and the residue chromatographed on silica eluting with mixtures of dichloromethane, methanol and concentrated ammonium hydroxide. The product containing fractions were combined and the solvent evaporated to give the title compound as a gum (1.13 g), Rf 0.1 (SS 4). N.M.R. δ(CDCl$_3$): 1.24 (3H,t), 1.48(2H,s), 2.61(2H,t), 2.73(2H,t), 2.90–2.98(4H,m), 3.93(2H,s), 4.14(2H,q), 6.88(2H,s), 6.91(1H,s), 6.96–7.03(2H,m), 7.12–7.18(2H,m).

EXAMPLE 1

Ethyl 3-[2-[(4-chlorophenyl)sulphonylamino]ethyl], 5-(4-fluorophenylmethyl)benzenepropanoate 4-chlorobenzenesulphonyl chloride (352 mg) was added portionwise to a stirred solution of ethyl 3-(2-aminoethyl)-5-[(4-fluorophenyl)methyl]benzenepropanoate (500 mg) and triethylamine (0.25 ml) in dry dichloromethane (5 ml) at room temperature. The solution was stirred at room temperature for 5 hours and then washed with water and dried (MgSO$_4$). The solvent was evaporated and the residue was chromatographed on silica gel. Elution with dichloromethane first gave impurity followed by pure product. The product fractions were combined and evaporated to give the title compound as an oil (560 mg); Rf 0.2 (SS 3). Found: C,62.08; H,5.47; N,2.73. C$_{26}$H$_{27}$ClFNO$_4$S requires C,61.96; H,5.40; N,2.78%.

EXAMPLE 2

3-[2-[(4-Chlorophenyl)sulphonylamino]ethyl]-5-[(4-fluorophenyl)methyl]benzenepropanoic acid A mixture of ethyl 3-[2-[(4-chlorophenyl)sulphonylamino]ethyl]-5-[(4-fluorophenyl)methyl]benzenepropanoate (500 mg), 2N sodium hydroxide solution (1.5 ml) and methanol (5 ml) was heated under reflux for 1 hour and then evaporated. The residue was dissolved in a small volume of water, and the solution was made acidic with 2N hydrochloric acid. The resulting mixture was extracted several times with ether and the combined extracts were dried (MgSO$_4$) and evaporated to give the title compound,(390 mg), m.p. 85°–87° C. Found: C,60.78A H,5.06; N,2.87. C$_{24}$H$_{33}$ClFNO$_4$S requires C,60.56; H,4.87; N,2.94%.

EXAMPLE 3

3-[2-[(4-Chlorophenyl)sulphonylamino]ethyl]-5-[(4-fluorophenyl)methyl]benzenepropanoic acid 2N sodium hydroxide solution (60 ml) was added to a stirred solution of ethyl 3-(2-carbamoylethyl)-5-[(4-fluorophenyl)methyl]benzenepropanoate (8.50 g) in dioxan (100 ml), and stirring was continued for 30 minutes at room temperature. The solution was cooled to 0° C. and sodium hypochlorite solution (15.2 ml of 14% solution) was added. The solution was stirred for 1 hour at 0° C., followed by 3 hours at room temperature and then 30 minutes at 100° C. It was then cooled to 0° C. and 4-chlorobenzenesulphonyl chloride (7.50 g) was added. The mixture was stirred for 2 hours, gradually allowing the temperature to reach room temperature. Further 4-chlorobenzenesulphonyl chloride (5.0 g) was added and the mixture was stirred for an additional 30 minutes and then acidified with concentrated hydrochloric acid. The mixture was diluted with water and extracted several times with diethyl ether. The combined ether extracts were washed with water, dried (MgSO$_4$) and evaporated, and the residue was chromatographed on silica gel. Elution was commenced with dichloromethane/methanol (99:1), gradually adjusting the ratio to 95:5. The product fractions were combined and evaporated and the residue was crystallised from ether/hexane to give the title compound (6.24 g),as a polymorph m.p. 107°–110° C. Found: C,60.94; H,5.05; N,2.91. C$_{23}$H$_{23}$ClFNO$_4$S requires: C,60.56; H,4.87; N,2.94%.

The following compounds were prepared similarly from the corresponding carboxamide-:

| Ex No | Structure | m.p. °C. | Analytical Data |
|---|---|---|---|
| 4 | phenyl-SO2-NH-CH2CH2-[3,5-disubstituted phenyl with 4-fluorobenzyl and CH2CH2CO2H] | 73–75 | Found: C, 65.26; H, 5.50: N, 3.33. $C_{24}H_{24}FNO_4S$, requires: C, 65.29; H, 5.48 N, 3.17% |
| 5 | 4-Br-phenyl-SO2-NH-CH2CH2-[3,5-disubstituted phenyl with 4-fluorobenzyl and CH2CH2CO3H] | 101–105 | Found: C, 55.46; H, 4.08; N, 2.46. $C_{24}H_{23}BrFNO_4S$ requires: C, 55.39; H, 4.45; N, 2.69% |
| 6 | 4-CF3-phenyl-SO2-NH-CH2CH2-[3,5-disubstituted phenyl with 4-fluorobenzyl and CH2CH2CO2H] | 135–138 | Found: C, 59.28; H, 4.54; N, 2.75. $C_{25}H_{23}F_4NO_4S$ requires: C, 58.93; H, 4.55; N, 2.75% |
| 7 | 2-naphthyl-SO2-NH-CH2CH2-[3,5-disubstituted phenyl with 4-fluorobenzyl and CH2CH2CO2H] | 115–119 | Found: C, 68.61; H, 5.36; N, 2.73. $C_{28}H_{26}FNO_4S$ requires: C, 68.41; H, 5.33; N, 2.85%. |
| 8 | 4-Cl-phenyl-SO2-NH-CH2CH2-[3,5-disubstituted phenyl with benzyl and CH2CH2CO2H] | 80–81 | Found: C, 63.07; H, 5.21; N, 2.71. $C_{24}H_{24}ClNO_4S$ requires: C, 62.94; H, 5.28; N, 3.06%. |
| 9 | 4-Cl-phenyl-SO2-NH-CH2CH2-[3,5-disubstituted phenyl with 2-fluorobenzyl and CH2CH2CO2H] | 102–103 | Found: C, 60.29; H, 5.24; N, 2.70. $C_{24}H_{23}ClFNO_4S$ requires: C, 60.56; H, 4.87; N, 2.94% |

| Ex No | Structure | m.p. °C. | Analytical Data |
|---|---|---|---|
| 10 | 4-ClC6H4-SO2-NH-CH2CH2-[3,5-disubst phenyl with CH2-(3-F-C6H4) and CH2CH2CO2H] | 128–129 | Found: C, 60.89; H, 4.98; N, 2.95. C$_{24}$H$_{23}$ClFNO$_4$S requires: C, 60.56; H, 4.87; N, 2.94%. |
| 11 | 4-ClC6H4-SO2-NH-CH2CH2-[3,5-disubst phenyl with CH2-(2-OMe-C6H4) and CH2CH2CO2H] | 98–102 | Found: C, 61.73; H, 5.31; N, 2.76. C$_{25}$H$_{26}$ClNO$_5$S requires: C, 61.53; H, 5.37; N, 2.87%. |
| 12 | 4-ClC6H4-SO2-NH-CH2CH2-[3,5-disubst phenyl with CH(CH3)-(4-F-C6H4) and CH2CH2CO2H] | gum | Found: C, 61.05; H, 5.46; N, 2.67. C$_{25}$H$_{25}$ClFNO$_4$S requires: C, 61.28; H, 5.14; N, 2.86%. |
| 13 | 4-ClC6H4-SO2-NH-CH2CH2-[3,5-disubst phenyl with C(=O)-(4-F-C6H4) and CH2CH2CO2H] | 127–129 | Found: C, 59.11; H, 4.23; N, 2.74% C$_{24}$H$_{21}$ClFNO$_5$S requires: C, 58.83; H, 4.32; N, 2.86%. |
| 14 | 4-ClC6H4-SO2-NH-CH2CH2-[3,5-disubst phenyl with O-(4-F-C6H4) and CH2CH2CO2H] | 107 | Found: C, 57.45; H, 4.34; N, 2.69. C$_{23}$H$_{21}$ClFNO$_5$S requires: C, 57.80; H, 4.43; N, 2.93. |

EXAMPLE 15

3-[2-[(4-Chlorophenyl)sulphonylamino]ethyl]-5-(4-methoxybenzoyl) benzenepropanoic acid A mixture of 3-[2-[(4-chlorophenyl)sulphonylamino]ethyl]-5-(4-fluorobenzoyl)benzenepropanoic acid (0.25 g) and potassium carbonate (0.212 g) in anhydrous methanol (5.0 ml) was heated under reflux for 18 hours. Additional potassium carbonate (0.212 g) was added and the mixture was heated under reflux for a further 20 hours and then cooled. Water (15 ml) was added and the solution was evaporated to about 10 ml and then acidified with 2N hydrochloric acid. The mixture was extracted several times with ethyl acetate and the combined extracts were washed with water and dried (MgSO$_4$). Evaporation of the solvent gave the title compound as a glass (0.22 g). Found: C,60.25; H,4.92; N,2.51. C$_{25}$H$_{24}$ClNO$_6$S requires C,59.81; H,4.82; N,2.79%.

EXAMPLE 16

3-[2-[(4-Chlorophenyl)sulphonylamino]ethyl]-5-(4-methylsulphonylbenzoyl)benzenepropanoic acid A solution of 3-[2-[(4-chlorophenyl)sulphonylamino]ethyl]-5-(4-fluorobenzoyl)benzenepropanoic acid (0.25 g) and sodium methanesulphinate (0.61 g) in dimethylsulphoxide (1.0 ml) was heated at 130° C. under dry nitrogen for 30 hours. Additional sodium methanesulphinate (1.2 g) was added and heating was continued for a further 20 hours. The solution was diluted with water, acidified with 2N hydrochloric acid and extracted several times with ethyl acetate. The combined extracts were washed with water, dried (MgSO$_4$) and evaporated. The residue was chromatographed on silica gel using dichloromethane/methanol (97:3) as eluent. The product fractions were combined and evaporated to give the title compound as a foam (0.115 g), Rf 0.25(SS 8). Found: C,54.96; H,4.53; N,2.18. $C_{25}H_{24}ClNO_7S_2$ requires: C,54.59; H,4.40; N,2.55%.

EXAMPLE 17

Ethyl 3-[2- [(4-chlorophenyl)sulphonylamino]ethyl-5-(4-fluorobenzoyl) benzenepropanoate A mixture of 3- [2-[(4-chlorophenyl)sulphonylamino]ethyl]-5-(4-fluorobenzoyl)benzenepropanoic acid (1.0 g), ethanol (25 ml) and concentrated sulphuric acid (5 drops) was stirred at room temperature for 72 hours. The resulting solution was evaporated to about one third volume and partitioned between ethyl acetate (100 ml) and saturated sodium bicarbonate solution (100 ml). The aqueous layer was separated, extracted with ethyl acetate, and the organic layers were combined, washed with water and dried (MgSO$_4$). Evaporation of the solvent gave an oil which was chromatographed on silica gel. Elution with dichloromethane followed by dichloromethane/methanol (50:1) gave the title compound as an oil (0.83 g). Rf 0.6 (SS 13), $\delta$(CDCl$_3$): 1.13(3H,t), 2.63(2H,t), 2.82(2H,t), 2.98(2H,t), 3.26(2H,m), 4.13(2H,q), 4.67(1H,t), 7.17–7.22(3H,m), 7.33(1H,s), 7.43–7.48(3H,m), 7.72–7.83(4H,m).

EXAMPLE 18

Ethyl 3-[2-[4-chlorophenyl)sulphonylamino]ethyl-5-(4-cyanobenzoyl)benzenepropanoate A solution of ethyl 3-[2-[(4-chlorophenyl)sulphonylamino]ethyl]-5-(4-fluorobenzoyl)benzenepropanoate (0.78 g) and potassium cyanide (0.39 g) in dry dimethylsulphoxide (5 ml) was heated at 150° C. for 17 hours. The solution was partitioned between ethyl acetate (100 ml) and water (100 ml), and sufficient solid sodium chloride was added to give a separation of the phases. The organic layer was separated, washed with water and dried (MgSO$_4$). The solvent was evaporated and the residue was chromatographed on silica gel. Elution with hexane/ethyl acetate (10:1) gradually adjusting the ratio to 2:1 gave the title compound as a gum (0.09 g), Rf 0.40 (SS 7). Found: C,61.99; H,4.71; N,5.07. $C_{27}H_{25}ClN_2O_5S$ requires C,61.77; H,4.80; N,5.36%.

EXAMPLE 19

3-[2-[(4-Chlorophenyl)sulphonylamino]ethyl]-5-(4-cyanobenzoyl)benzenepropanoic acid 1N Sodium hydrochloride solution (0.6 ml) was added to a solution of ethyl 3-[2-[4-chlorophenyl)sulphonylamino]ethyl]-5-(4-cyanobenzoyl)benzenepropanoate (0.15 g) in ethanol 5 ml, and the solution was stirred at room temperature for 4 hours. Further 1N sodium hydroxide solution (0.4 ml). was added, and stirring was continued for another 17 hours. The solution was diluted with water (35 ml), acidified with 2N hydrochloric acid and extracted three times with dichloromethane. The combined extracts were dried (MgSO$_4$) and evaporated, and the residue was chromatographed on silica gel. The column was eluted with dichloromethane/methanol/acetic acid (99:1:0.1) to give a gum which was rechromatographed on silica gel using hexane/ethyl acetate/acetic acid (100:50:2) to give the title compound as a gum (0.055 g), Rf 0.20 (SS 14). Found: C,60.53; H,4.21; N,5.07. $C_{25}H_{21}ClN_2O_5S$ requires C,60.42; H,4.26; N,5.64%.

EXAMPLE 20

3-[2-[(4-Chlorophenyl)sulphonylamino]ethyl]-5-[(4-methoxyphenyl)methyl]benzenepropanoic acid A solution of 3-[2-[(4-chlorophenyl)sulphonyl]amino] ethyl]-5-(4-methoxybenzoyl)benzenepropanoic acid (0.95 g) and triethylsilane (1.20 ml) in trifluoroacetic acid (20 ml) was stirred at room temperature for 18 hours and then evaporated. The residue was triturated with diethyl ether and the mixture was filtered to give the title compound (0.81 g), m.p. 106°–108° C. Found: C,61.68; H,5.02; N,2.91. $C_{25}H_{26}ClNO_5S$ requires C,61.53; H,5.37; N,2.87%.

EXAMPLE 21

3-[2-[(4-Chlorophenyl)sulphonylamino]ethyl-5-[(4-methylsulphonylphenyl)methyl]benzenepropanoic acid Treatment of 3-[2-[(4-chlorophenyl)sulphonylamino]ethYl]-5-(4-methylsulphonylbenzoyl)benzenepropanoic acid (0.825 g) with triethysilane (0.96 ml) in trifluoroacetic acid (15 ml) according to the method of Example 20 gave the title compound (0.51 g), m.p. 105°–107° C. Found: C,55.84; H,4.87; N,2.45. $C_{25}H_{26}ClNO_6S_2$ requires C,56.01; H,4.89; N,2.61%.

EXAMPLE 22

3-[2-[(4-Chlorophenyl)sulphonylamino]ethyl]-5-[(4-fluorophenyl)hydroxymethyl]benzenepropanoic acid Sodium borohydride (0.077 g) was added portionwise to a suspension of 3-[2-[(4-chlorophenyl)sulphonylamino]ethyl]-5-(4-fluorobenzoyl)benzenepropanoic acid (0.50 g) in ethanol (12 ml), and the resulting solution was stirred at room temperature for 18 hours. 2N hydrochloric acid (5 ml) was added dropwise followed by ethyl acetate (50 ml), and the mixture was stirred for 1 hour. The organic layer was separated, washed with water and dried (MgSO$_4$). The solvent was evaporated and the residue was chromatographed on silica gel. The column was eluted with hexane/ethyl acetate (5:1), followed by hexane/ethyl acetate/acetic acid (50:50:1), gradually increasing the polarity to give a ratio of 10:90:1. The product fractions were combined and evaporated to give the title compound as a gum (0.36 g), Rf 0.45 (SS 15). Found: C,58.58; H,4.71; N,2.65. $C_{24}H_{23}ClFNO_5S$ requires C,58.59; H,4.71; N,2.85%.

EXAMPLE 23

Ethyl 3-[2-[Z-2-(4-chlorophenyl)cycloprop-1-ylcarboxamido]ethyl]-5-[(4-fluorophenyl)methyl]-benzenepropanoate 1-(3-dimethylaminopropyl)-3-ethylcarbodiimide hydrochloride (0.575 g) was added to a solution of ethyl 3-(2-aminoethyl)-5-[(4-fluorophenyl)methyl]benzenepropanoate (0.50 g), Z-2-(4-chlorophenyl)-cyclopropane-1-carboxylic acid (EP 487,095) (0,295 g), 1-hydroxybenzotriazole hydrate (0,203 g) and N,N-diisopropylethylamine (0.194 g) in dry dichloromethane (5 ml), and the solution was allowed to stand at room temperature overnight. The solution was washed with water, dried ($MgSO_4$) and evaporated. The residue was chromatographed on silica gel using dichloromethane as eluent, gradually increasing the polarity to dichloromethane/methanol (99:1). The product fractions were combined and evaporated to give the title compound as a gum (0.69 g), Rf 0.15 (SS 2). Found: C,70.85; H,6.08; N,2.71. $C_{30}H_{31}ClFNO_3$ requires C,70.82; H,6.15; N,2.76%

EXAMPLE 24

3-[2-[Z-2-(4-Chlorophenyl)cycloprop-1-ylcarboxamido]ethyl]-5-[(4-fluorophenyl)methyl]benzenepropanoic acid Hydrolysis of ethyl 3-[2-[Z-2-(4-chlorophenyl)-cycloprop-1-ylcarboxamido]ethyl]-5-[(4-fluorophenyl)methyl] benzenepropanoate (0.60 g) according to the method of Example 2 gave the title compound as a gum (0.507 g), Rf 0.7 (SS 5). Found: C,69.99; H,5.88; N,2.84, $C_{28}H_{27}ClFNO_3$ requires C,70.07; H,5.67; N,2.92%.

EXAMPLE 25

Pharmaceutical Capsules

|  | mg/capsule |
|---|---|
| Thromboxane $A_2$ Antagonist | 25.0 |
| Thromboxane Synthetase Inhibitor | 150.0 |
| Starch | 74.0 |
| Magnesium stearate BP | 1.0 |
|  | 250 mg |

The thromboxane $A_2$ antagonist and the thromboxane synthetase inhibitor are sieved and blended with the starch and the excipients. The mix is filled into size No 2 hard gelatin capsules, using suitable machinery. Capsules of other strengths or with different ratios of active ingredients may be prepared in a similar manner.

We claim:
1. A compound having the formula-:

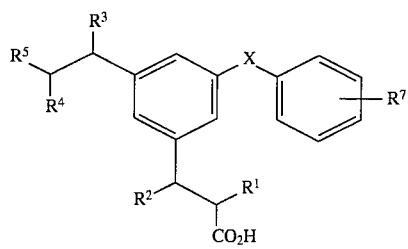

and pharmaceutically acceptable salts and biolabile esters thereof, wherein $R^1$, $R^2$ $R^3$ and $R^4$ are each independently H or $C_1$–$C_4$ alkyl;

$R^5$ is $(CH_2)_m NHSO_2 R^6$ or $(CH_2)_m NHCOR^6$;

$R^6$ is $C_1$–$C_6$ alkyl, $C_3$–$C_6$ cycloalkyl optionally substituted by aryl, aryl or heteroaryl; wherein aryl means phenyl or naphthyl and heteroaryl means furyl, thienyl, or pyridyl, any of which ring systems may optionally be substituted with from one to three substituents each independently chosen from $C_1$–$C_4$ alkyl, $C_1$–$C_4$ alkoxy, halo, $CF_3$, $OCF_3$ and CN;

$R^7$ represents from one to three substituents each independently selected from H, $C_1$–$C_4$ alkyl, $C_1$–$C_4$ alkoxy, halo, $CF_3$, $OCF_3$, CN, $CONH_2$, and $S(O)_n(C_1$–$C_4$ alkyl);

X is $CH_2$, $CHCH_3$, CH(OH), $CH(OH)CH_3$, $C=CH_2$, CO, or O;

m is 0 or 1; and n is 0, 1 or 2.

2. A compound as claimed in claim 1 wherein $R^1$, $R^2$, $R^3$ and $R^4$ are each H, $R^5$ is $NHSO_2R^6$ and X is $CH_2$, $CH(CH_3)$, CO or O.

3. A compound as claimed in claim 2 wherein $R^5$ is $NHSO_2R^6$ and $R^6$ is phenyl substituted by halo or $CF_3$.

4. A compound as claimed in claim 3 wherein $R^6$ is 4-chlorophenyl.

5. A compound as claimed in claim 4 wherein $R^7$ is H, F, $OCH_3$, $SO_2CH_3$ or CN.

6. A compound as claimed in claim 5 wherein the biolabile ester is the methyl, ethyl or t-butyl ester.

7. A compound as claimed in claim 1 wherein said compound is selected from-:

3-[(4-fluorophenyl)methyl]-5-[2-[(4-trifluoromethylphenyl)sulphonylamino]ethyl]benzenepropanoic acid;

3-[2-[(4-chlorophenyl)sulphonylamino]ethyl]-5-[1-(4-fluorophenyl) ethyl]benzenepropanoic acid;

3-[2-[(4-chlorophenyl)sulphonylamino]ethyl]-5-[(4-fluorophenyl)methyl]benzenepropanoic acid;

3-[2-[(4-chlorophenyl)sulphonylamino]ethyl]-5-(4-fluorophenoxy)benzenepropanoic acid;

3-[2-[(4-chlorophenyl)sulphonylamino]ethyl]-5-(4-methoxybenzoyl)benzenepropanoic acid; and 3-[2-[(4-chlorophenyl)sulphonylamino]ethyl]-5-(4-cyanobenzoyl)benzenepropanoic acid.

8. A pharmaceutical composition comprising a compound of the formula (I), or a pharmaceutical acceptable salt or biolabile ester thereof as claimed in claim 1, together with a pharmaceutically acceptable diluent or carrier.

9. A pharmaceutical composition as claimed in claim 8 which also contains a thromboxane synthetase inhibitor.

10. A pharmaceutical composition as claimed in claim 9 wherein said thromboxane synthetase inhibitor is selected from-:

4-[2-(1H-imidazol-1-yl)ethoxy]benzoic acid, 3-(1H-imidazol-1-ylmethyl)-2-methyl-1H-indole-1-propanoic acid, 2-methyl-3-(3-pyridylmethyl)-1H-indole-1-propanoic acid, 3-methyl-2-(3-pyridylmethyl)benzo-[b]thiophene-5-carboxylic acid, 1,3-dimethyl-2-(1H-imidazol-1-ylmethyl)-1H-indol-5-carboxylic acid, 2-methyl-3-(3-pyridyl)-1H-indole-1-pentanoic acid.

11. A pharmaceutical composition as claimed in claim 10 wherein said thromboxane synthetase inhibitor is 2-methyl-3-(3-pyridyl)-1H-indole-1-pentanoic acid.

12. A method of treating a patient suffering from a disease condition in which thromboxane $A_2$ is the causative agent, which comprises administering to said patient an effective amount of a compound of the formula (I) as claimed in claim 1 optionally together with a thromboxane synthetase inhibitor.

13. The method as recited in claim 12 wherein the disease condition is atherosclerosis or unstable angina and for preventing reocclusion after percutaneous transluminal angioplasty.

14. A compound of the formula-:

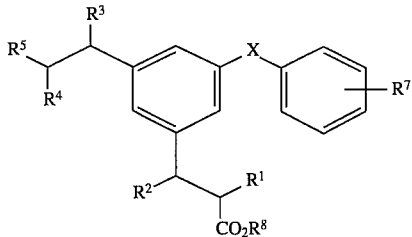
(II)

where $R^1$, $R^2$, $R^3$, $R^4$, $R^5$, $R^7$, and X are as defined in claim 1, and $R^8$ is $C_1$–$C_4$ alkyl.

15. A compound of the formula

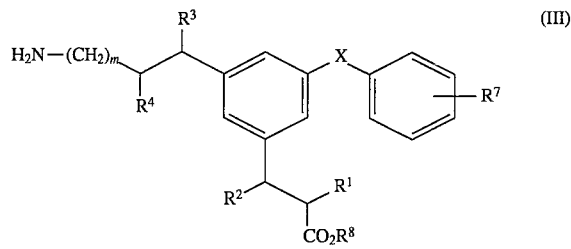
(III)

where $R^1$, $R^2$, $R^3$, $R^4$, $R^7$, m, and X are as defined in claim 1 and $R^8$ is $C_1$–$C_4$ alkyl.

16. A compound of the formula

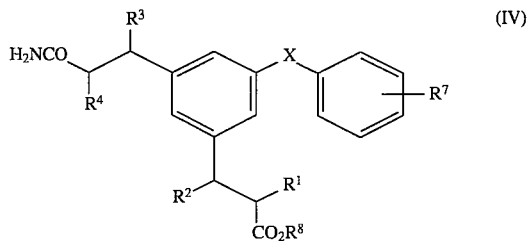
(IV)

wherein $R^1$, $R^2$, $R^3$, $R^4$, R, $R^7$ and X are as defined in claim 1 and $R^8$ is $C_1$–$C_4$ alkyl.

17. 2-Methyl-3-(3-pyridyl)-1H-indole-1-pentanoic acid.

* * * * *